United States Patent
Olde et al.

(10) Patent No.: US 9,612,182 B2
(45) Date of Patent: Apr. 4, 2017

(54) METHOD AND DEVICE FOR DETECTING A FAULT CONDITION

(75) Inventors: Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 517 days.

(21) Appl. No.: 13/519,248

(22) PCT Filed: Dec. 22, 2010

(86) PCT No.: PCT/EP2010/070549
§ 371 (c)(1),
(2), (4) Date: Aug. 30, 2012

(87) PCT Pub. No.: WO2011/080187
PCT Pub. Date: Jul. 7, 2011

(65) Prior Publication Data
US 2013/0204174 A1    Aug. 8, 2013

Related U.S. Application Data

(60) Provisional application No. 61/290,305, filed on Dec. 28, 2009.

(30) Foreign Application Priority Data

Dec. 28, 2009   (SE) ........................................ 0951024

(51) Int. Cl.
*A61M 1/36* (2006.01)
*G01N 11/02* (2006.01)
*A61M 5/168* (2006.01)

(52) U.S. Cl.
CPC ........... *G01N 11/02* (2013.01); *A61M 1/3653* (2013.01); *A61M 1/3656* (2014.02);
(Continued)

(58) Field of Classification Search
CPC ...... A61M 5/16859; A61M 2205/3331; A61M 5/14228
(Continued)

(56) References Cited

U.S. PATENT DOCUMENTS 5,100,374 A * 3/1992 Kageyama .......... A61M 1/1086
600/16
5,906,589 A * 5/1999 Gordon et al. .................. 604/65
(Continued)

FOREIGN PATENT DOCUMENTS

DE    197 34 002    9/1998
DE    199 01 078    2/2000
(Continued)

OTHER PUBLICATIONS

Jammu et al., "Condition Monitoring of Rotary Blood Pump", 1997, ASAIO Journal M639-643.*
(Continued)

*Primary Examiner* — Regis Betsch
(74) *Attorney, Agent, or Firm* — Mueting, Raasch & Gebhardt, P.A.

(57) ABSTRACT

A device and method for detecting fault conditions in a fluid connection system between a first fluid containing system including a first pulse generator (e.g., an extracorporeal blood circuit) and a second fluid containing system including a second pulse generator (e.g., a human or animal vascular system). A pressure sensor detects first pulses from the first pulse generator and second pulses from the second pulse generator. A time-dependent monitoring signal based on data obtained from said pressure sensor is generated and processed to calculate a parameter value indicative of the shape of at least part of a first pulse in the monitoring signal. The parameter value is evaluated to detect the fault condition. The fault condition may involve disconnection of an
(Continued)

access device; reversed connection of access devices; occlusion of the fluid path through an access device; or infiltration in tissue surrounding an access point in the vascular system.

29 Claims, 13 Drawing Sheets

(52) U.S. Cl.
CPC ....... *A61M 1/3639* (2013.01); *A61M 5/16859* (2013.01); *A61M 2205/13* (2013.01); *A61M 2205/15* (2013.01); *A61M 2205/3331* (2013.01); *A61M 2230/04* (2013.01)

(58) Field of Classification Search
USPC .......................................................... 702/35
See application file for complete search history.

(56) References Cited

U.S. PATENT DOCUMENTS

| | | | | |
|---|---|---|---|---|
| 6,077,443 | A * | 6/2000 | Goldau | A61M 1/16 210/143 |
| 6,090,048 | A * | 7/2000 | Hertz | A61M 5/16859 600/485 |
| 6,623,443 | B1 | 9/2003 | Polaschegg | |
| 6,731,216 | B2 * | 5/2004 | Ho | A61M 5/14228 340/591 |
| 8,430,834 | B2 * | 4/2013 | Kopperschmidt | 604/6.11 |
| 8,574,183 | B2 * | 11/2013 | Kopperschmidt | 604/5.04 |
| 8,715,216 | B2 * | 5/2014 | Olde et al. | 604/6.11 |
| 2005/0010118 | A1 | 1/2005 | Toyoda | |
| 2010/0234787 | A1 | 9/2010 | Masaoka | |
| 2011/0040502 | A1 * | 2/2011 | Furmanski et al. | 702/51 |
| 2012/0283581 | A1 | 11/2012 | Olde et al. | |
| 2013/0204174 | A1 * | 8/2013 | Olde et al. | 604/6.11 |
| 2013/0204542 | A1 * | 8/2013 | Olde et al. | 702/35 |

FOREIGN PATENT DOCUMENTS

| | | | | |
|---|---|---|---|---|
| DE | 10355042 | B3 * | 6/2005 | ............. A61M 1/16 |
| EP | 0 328 162 | | 8/1989 | |
| WO | WO 97/10013 | | 3/1997 | |
| WO | WO 9710013 | A1 * | 3/1997 | ............. A61M 5/168 |
| WO | WO 2009/038834 | | 3/2009 | |
| WO | WO 2009/060741 | | 5/2009 | |
| WO | WO 2009/127683 | | 10/2009 | |
| WO | WO 2009127683 | A1 * | 10/2009 | ............. G01M 3/28 |
| WO | WO 2009/031560 | | 12/2009 | |
| WO | WO 2009156174 | A3 * | 5/2010 | |
| WO | WO 2010/149726 | | 12/2010 | |
| WO | WO 2011080187 | A1 * | 7/2011 | |

OTHER PUBLICATIONS

Kim et al., "Noninvasive Diagnosis of Mechanical Failure of the Implanted Total Artificial Heart Using Neural Network Analysis of Acoustic Signals", 1995, ASAIO Journal: Jul./Aug./Sep. 1995.*

* cited by examiner

METHOD AND DEVICE FOR DETECTING A FAULT CONDITION

This application is a U.S. National Stage Application of International Application No. PCT/EP2010/070549, filed Dec. 22, 2010, which was published in English on Jul. 7, 2011 as International Patent Publication WO 2011/080187 A1, and which claims the benefit under 35 U.S.C. 119(e) of U.S. Provisional Application No. 61/290,305 filed Dec. 28, 2009. International Application No. PCT/EP2010/070549 also claims priority to Swedish Application No. 0951024-9 filed Dec. 28, 2009.

TECHNICAL FIELD

The present invention generally relates to monitoring of fault conditions in a fluid containing system, based on measurement data obtained from one or more pressure sensors in the fluid containing system. The present invention is e.g. applicable in arrangements for extracorporeal blood treatment.

BACKGROUND ART

In extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or catheters, which are inserted into a blood vessel access. Such extracorporeal blood treatments include hemodialysis, hemodiafiltration, hemofiltration, plasmapheresis, blood fraction separation (e.g. cells) of donor blood, etc.

In extracorporeal blood treatment, it is vital to minimize the risk for malfunctions in the extracorporeal blood flow circuit, since these may lead to a potentially life-threatening condition of the patient. Serious conditions may arise if the extracorporeal blood flow circuit is disrupted, e.g. by an access device for blood extraction (e.g. an arterial needle/catheter) coming loose from the blood vessel access, causing air to be sucked into the circuit which leads to air embolism in the patient and increased risk of clotting in the circuit, or by an access device for blood reintroduction (e.g. a venous needle/catheter) coming loose from the blood vessel access, causing the patient to be drained of blood within minutes. Other malfunctions may be caused by the blood vessel access becoming blocked or obstructed, by the access device being positioned too close to the walls of the blood vessel access, or by constriction/occlusion of the access device due to clotting.

These malfunctions all originate in a "connection system" between the patient and the extracorporeal blood flow circuit. The connection system includes one or more access devices and possibly one or more releasable connectors for attaching the access devices to tubing in the extracorporeal blood flow circuit.

An apparatus for extracorporeal blood treatment may include one or more surveillance devices that monitor the integrity of the blood flow circuit and issue an alarm and/or cause appropriate action to be taken whenever a potentially dangerous situation is detected. Such surveillance devices may operate on measurement signals from one or more pressure sensors in the circuit. Conventionally, the monitoring during a blood treatment is carried out by comparing one or more measured average pressure levels with one or more threshold values and/or by monitoring the presence of air bubbles using an air detector in the circuit. For example, failure in the blood extraction may involve air being introduced into the circuit, whereby the measured average pressure may approach atmospheric pressure, or the blood flow being blocked or obstructed, whereby the measured average pressure may drop to a low level. A failure in the reintroduction of blood into the blood vessel access due to a failure in the connection system may be detectable as a decrease in the measured average pressure. However, it may be difficult to set appropriate threshold values, since the average pressure in the circuit may vary between treatments, and also during a treatment, e.g. as a result of the patient moving. Further, if an access device comes loose and gets stuck in bed sheets or the patient's clothes, the measured average pressure might not change enough to indicate the potentially dangerous situation.

To increase the monitoring precision, WO 97/10013 proposes detecting, as one of several options, a heart signal in the measured pressure and using the heart signal as an indicator of the integrity of a fluid connection between an extracorporeal blood flow circuit and a blood vessel access. The heart signal represents a pressure wave which is produced by the patient's heart and transmitted from the patient's circulatory system to the extracorporeal blood flow circuit via the blood vessel access. Malfunctions in the fluid connection will disturb the transmission of the heart-generated pressure wave to the circuit, causing the heart signal to change or even disappear. The measured pressure may also include a strong pressure wave produced by the blood pump in the extracorporeal blood flow circuit. In WO 97/10013, the monitoring involves filtering a measured pressure signal to remove the frequency components that originate from the blood pump, and then detecting the heart signal by analysing the filtered pressure signal. The amplitude of the filtered pressure signal is then taken as an indication of the integrity of the fluid connection.

US2005/0010118 proposes a solution which involves applying a frequency analysis to a measured pressure signal to generate a frequency spectrum, and monitoring anomalies of the fluid connection based on the intensity of the frequency component caused by the patient's heartbeat. US2005/0010118 proposes various solutions on how to identify only the frequency component caused by the patient's heartbeat in the frequency spectrum, which consists of a mixture of various frequency components, including those caused by pumps in the extracorporeal blood flow circuit. The proposed solutions all involve a subtraction of a reference frequency spectrum from the frequency spectrum obtained from the pressure signal. The reference frequency spectrum may be obtained from the pressure signal prior to installation of the fluid connection, may be synthesized based on the operating frequency of the pumps, or may be obtained from the pressure signal at a earlier point in time. Irrespective of solution, the result of the subtraction is processed for extraction of a parameter value that represents the intensity of the frequency component caused by the patient's heartbeat. If the parameter value falls below an threshold value, an anomaly of the fluid connection is deemed to have occurred.

The prior art also comprises WO2009/127683, which discloses a technique for monitoring the integrity of an the extracorporeal blood flow circuit in fluid communication with a blood vessel of a patient, by isolating a beating signal in a pressure signal obtained from a pressure sensor in the extracorporeal blood flow circuit. The beating signal manifests itself as an amplitude modulation of the pressure signal and is formed by interference between pressure waves generated by the patient's heart and pressure waves generated by a pumping device in the extracorporeal blood flow circuit. Absence of the beating signal is taken as an indication that the integrity of the circuit is compromised.

Corresponding needs to monitor the integrity of a connection system between first and second fluid containing systems may arise in other fields of technology.

Still further, there may be a need for techniques allowing other types of fault conditions to be identified in a connection system between first and second fluid containing systems in general, and between vascular systems and in extracorporeal blood flow circuits in particular.

SUMMARY

It is an object of the invention to at least partly overcome one or more of the above-identified limitations of the prior art. Specifically, it is an object to provide an alternative or complementary technique for monitoring the integrity of a connection system between first and second fluid containing systems using a pressure measurement, preferably with an improved robustness and/or an increased certainty of detecting a malfunction in the connection system.

It is also an object to provide a technique for monitoring further fault conditions in such a connection system.

This and other objects, which will appear from the description below, are at least partly achieved by means of methods, devices, and computer program products according to the independent claims, embodiments thereof being defined by the dependent claims.

A first aspect of the invention is a method for detecting a fault condition in a fluid connection system between first and second fluid containing systems, wherein the first fluid containing system comprises a first pulse generator, and the second fluid containing system comprises a second pulse generator, and wherein at least one pressure sensor is arranged in the first fluid containing system to detect first pulses originating from the first pulse generator and second pulses originating from the second pulse generator, said method comprising: generating a time-dependent monitoring signal based on measurement data obtained from said at least one pressure sensor, such that the monitoring signal at least comprises one or more first pulses; processing the monitoring signal to calculate a parameter value which is indicative of the shape of at least part of a first pulse in the monitoring signal, and evaluating the parameter value for detection of said fault condition.

A second aspect of the invention is a computer program product comprising instructions for causing a computer to perform the method of the first aspect.

A third aspect of the invention is a device for detecting a fault condition in a fluid connection system between first and second fluid containing systems, wherein the first fluid containing system comprises a first pulse generator, and the second fluid containing system comprises a second pulse generator, and wherein at least one pressure sensor is arranged in the first fluid containing system to detect first pulses originating from the first pulse generator and second pulses originating from the second pulse generator, said device comprising: means for generating a time-dependent monitoring signal based on measurement data obtained from said at least one pressure sensor, such that the monitoring signal at least comprises one or more first pulses; means for processing the monitoring signal to calculate a parameter value which is indicative of the shape of at least part of a first pulse in the monitoring signal, and means for evaluating the parameter value for detection of said fault condition.

A fourth aspect of the invention is a device for detecting a fault condition in a fluid connection system between first and second fluid containing systems, wherein the first fluid containing system comprises a first pulse generator, and the second fluid containing system comprises a second pulse generator, and wherein at least one pressure sensor (is arranged in the first fluid containing system to detect first pulses originating from the first pulse generator and second pulses originating from the second pulse generator, said device comprising: an input for obtaining measurement data from said at least one pressure sensor, and a signal processor connected to said input and being configured to generate a time-dependent monitoring signal based on the measurement data such that the monitoring signal at least comprises one or more first pulses, to process the monitoring signal for calculation of a parameter value which is indicative of the shape of at least part of a first pulse in the monitoring signal, and to evaluate the parameter value for detection of said fault condition.

A fifth aspect of the invention is a method for detecting a fault condition in a pumping device included in an extracorporeal blood treatment system, wherein the extracorporeal blood treatment system is adapted for connection to a vascular system of a subject such that the pumping device pumps blood from the vascular system through a blood treatment device back to the vascular system, and wherein at least one pressure sensor is arranged in the extracorporeal blood treatment system to detect first pulses originating from the pumping device and second pulses originating from a physiological pulse generator in the subject, said method comprising: generating a time-dependent monitoring signal based on measurement data obtained from said at least one pressure sensor, such that the monitoring signal comprises one or more first pulses and no second pulses; processing the monitoring signal to calculate a parameter value which is indicative of the shape of at least part of a first pulse in the monitoring signal; and evaluating the parameter value for detection of said fault condition.

A sixth aspect of the invention is a computer program product comprising instructions for causing a computer to perform the method of the sixth aspect.

An seventh aspect of the invention is a device for detecting a fault condition in a pumping device included in an extracorporeal blood treatment system, wherein the extracorporeal blood treatment system is adapted for connection to a vascular system of a subject such that the pumping device pumps blood from the vascular system through a blood treatment device back to the vascular system, and wherein at least one pressure sensor is arranged in the extracorporeal blood treatment system to detect first pulses originating from the pumping device and second pulses originating from a physiological pulse generator in the subject, said device comprising: means for generating a time-dependent monitoring signal based on measurement data obtained from said at least one pressure sensor, such that the monitoring signal comprises one or more first pulses and no second pulses; means for processing the monitoring signal to calculate a parameter value which is indicative of the shape of at least part of a first pulse in the monitoring signal; and means for evaluating the parameter value for detection of said fault condition.

An eighth aspect of the invention is a device for detecting a fault condition in a pumping device included in an extracorporeal blood treatment system, wherein the extracorporeal blood treatment system is adapted for connection to a vascular system of a subject such that the pumping device pumps blood from the vascular system through a blood treatment device back to the vascular system, and wherein at least one pressure sensor is arranged in the extracorporeal blood treatment system to detect first pulses originating from the pumping device and second pulses originating from a physiological pulse generator in the subject, said device comprising: an input for obtaining measurement data from said at least one pressure sensor, and a signal processor connected to said input and being configured to generate a time-dependent monitoring signal based on measurement data obtained from said at least one pressure sensor, such that the monitoring signal comprises one or more first pulses and no second pulses, to process the monitoring signal to calculate a parameter value which is indicative of the shape of at least part of a first pulse in the monitoring signal, and to evaluate the parameter value for detection of said fault condition.

Still other objectives, features, aspects and advantages of the present invention will appear from the following detailed description, from the attached claims as well as from the drawings.

BRIEF DESCRIPTION OF THE DRAWINGS

Embodiments of the invention will now be described in more detail with reference to the accompanying schematic drawings.

DETAILED DESCRIPTION OF EXEMPLARY EMBODIMENTS

Figure 1:
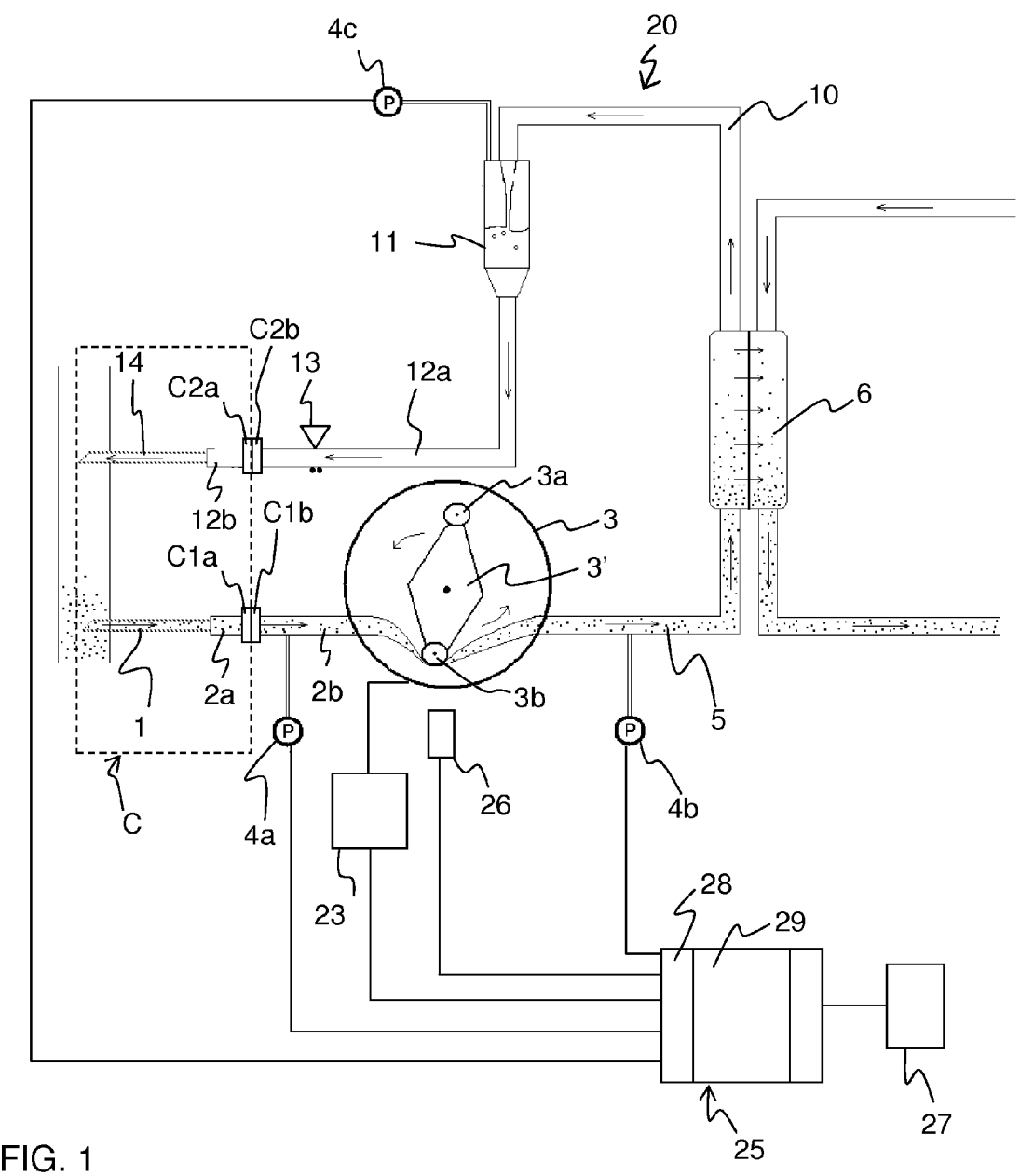
FIG. 1 is a schematic view of a system for hemodialysis treatment including an extracorporeal blood flow circuit.

In the following, different embodiments for fault detection will be described with reference to an extracorporeal blood flow circuit included in a dialysis machine. It is to be understood that corresponding embodiments may be implemented in other types of fluid containing systems, as exemplified at the end of the description.

Throughout the following description, like elements are designated by the same reference numerals.

I. Example of Extracorporeal Circuit

FIG. 1 shows an example of an extracorporeal blood flow circuit 20 of the type which is used for dialysis. The extracorporeal blood flow circuit 20 is connected to the vascular system of a patient by means of a connection system C. The connection system C comprises an arterial access device 1 for blood extraction (here in the form of an arterial needle), a connection tube segment 2$a$ and a connector C1$a$. The connection system C also comprises a venous access device 14 for blood reintroduction (here in the form of a venous needle), a connection tube segment 12$b$, and a connector C2$a$. The connectors C1$a$, C2$a$ are arranged to provide a releasable or permanent engagement with a corresponding connector C1$b$, C2$b$ in the circuit 20 so as to form a blood path between the circuit 20 and the arterial needle 1 and the venous needle 14, respectively. The connectors C1$a$, C1$b$, C2$a$, C2$b$ may be of any known type.

In the illustrated example, the extracorporeal circuit 20 comprises the connector C1$b$, an arterial tube segment 2$b$, and a blood pump 3 which may be of peristaltic type, as indicated in FIG. 1. At the inlet of the pump there is a pressure sensor 4$a$ (hereafter referred to as "arterial sensor") which measures the pressure before the pump in the arterial tube segment 2$b$. The blood pump 3 forces the blood, via a tube segment 5, to the blood-side of a dialyser 6. Many dialysis machines are additionally provided with a pressure sensor 4$b$ that measures the pressure between the blood pump 3 and the dialyser 6. The blood is led via a tube segment 10 from the blood-side of the dialyser 6 to a venous drip chamber or deaeration chamber 11 and from there back to the connection system C via a venous tube segment 12$a$ and the connector C2$b$. A pressure sensor 4$c$ (hereafter referred to as "venous sensor") is provided to measure the pressure on the venous side of the dialyser 6. In the illustrated example, the venous sensor 4$c$ measures the pressure in the venous drip chamber 11. Both the arterial needle 1 and the venous needle 14 are connected to the vascular system of a human or animal patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

Herein, the "venous side" of the extracorporeal circuit 20 refers to the part of the blood path located downstream of the blood pump 3, whereas the "arterial side" of the extracorporeal circuit 20 refers to the part of the blood path located upstream of the blood pump 3. In the example of FIG. 1, the venous side is made up of tube segment 5, the blood-side of the dialyser 6, tube segment 10, drip chamber 11 and tube segment 12a, and the arterial side is made up of tube segment 2b.

In FIG. 1, a control unit 23 is provided, inter alia, to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Further, in FIG. 1, a surveillance/monitoring device 25 is configured to monitor proper operation of the circuit 20, specifically by processing a measurement signal obtained from one or more of the pressure sensors 4a-4c. The detection of a fault condition may bring the device 25 to activate an alarm and/or stop the blood flow, e.g. by stopping the blood pump 3 and activating one or more clamping devices 13 (only one shown) on the tube segments 2a, 2b, 5, 10, 12a, 12b.

As indicated in FIG. 1, the device 25 may also be connected to the control unit 23. Alternatively or additionally, the device 25 may be connected to a pump sensor 26, such as a rotary encoder (e.g. conductive, optical or magnetic) or the like, for indicating the frequency and/or phase of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In the various embodiments described herein, pulse generators in the patient and the extracorporeal blood flow circuit generate pressure waves which propagate in the liquid system extending from the respective pulse generator to a pressure sensor, which is in direct or indirect hydrostatic contact with the liquid system. A "pressure wave" is a mechanical wave in the form of a disturbance that travels or propagates through a material or substance. The pressure waves typically propagate in the liquid system at a velocity of about 3-20 m/s. The pressure sensor generates measurement data that forms a pressure pulse for each pressure wave. A "pressure pulse" or "pulse" is thus a set of data samples that define a local increase or decrease (depending on implementation) in signal magnitude within a time-dependent measurement signal ("pressure signal"). The pressure pulses appear at a rate proportional to the generation rate of the pressure waves at the pulse generator. The pressure sensor may be of any type, e.g. operating by resistive, capacitive, inductive, magnetic or optical sensing, and using one or more diaphragms, bellows, Bourdon tubes, piezo-electrical components, semiconductor components, strain gauges, resonant wires, photo-plethysmography (PPG), accelerometers, bioimpedance, etc.

In FIG. 1, the surveillance device 25 comprises a data acquisition part 28 for sampling measurement data from the pressure sensor(s) 4a-4c and, optionally, for pre-processing the pressure signal that is formed by the sampled measurement data. For example the data acquisition part 28 may include an A/D converter with a required minimum sampling rate and resolution, one or more signal amplifiers, one or more filters to remove undesired signal components in the measurement data, such as offset, high frequency noise and supply voltage disturbances. Generally, the measurement data is a time sequence of data samples, each representing an instantaneous pressure of the blood in the circuit at the location of the relevant pressure sensor 4a-4c. The pre-processing in the data acquisition part 28 results in a monitoring signal, which is provided as input to a data analysis part 29 that executes the actual monitoring process. Depending on implementation, the surveillance device 25 may use digital components or analog components, or a combination thereof, for acquiring, processing and analysing the measurement data.

FIG. 2(a) shows an example of a pressure signal in the time domain, and FIG. 2(b) shows the corresponding energy spectral density, i.e. signal amplitude as a function of frequency. The energy spectral density reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pressure waves in the extracorporeal blood flow circuit. For example, in a peristaltic pump of the type shown in FIG. 1, two pump strokes are generated for each full revolution of the rotor 3', i.e. one pump stroke for each roller 3a, 3b. FIG. 2(b) also indicates the presence of a frequency component at half the pumping frequency ($0.5f_0$) and harmonics thereof, in this example at least $f_0$, $1.5f_0$, $2f_0$ and $2.5f_0$. FIG. 2(b) also shows a heart signal (at 1.1 Hz) which in this example is approximately 40 times weaker than the blood pump signal at the base frequency $f_0$.

Figure 2:
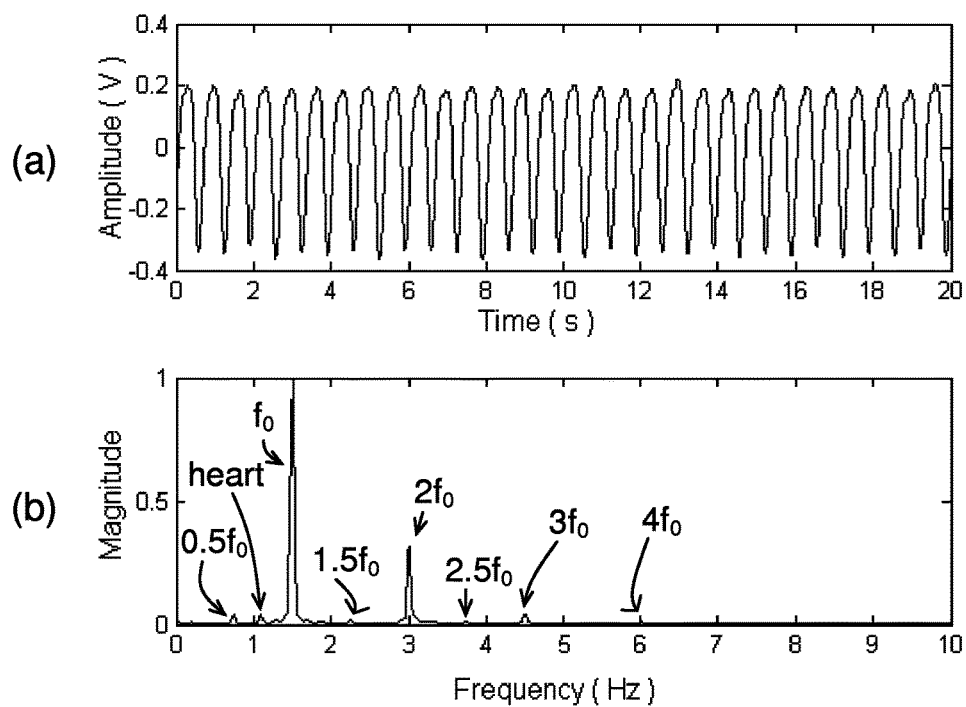
FIG. 2($a$) is a plot in the time domain of a pressure signal containing both pump frequency components and a heart signal, and FIG. 2($b$) is a plot of the corresponding signal in the frequency domain.

Although not shown in FIG. 2, the pressure signal may also contain repetitive pressure pulses originating from other mechanical pulse generators (not shown) in the circuit 20, such a valves, a pump for dialysis fluid, etc. Repetitive pressure pulses may also originate from mechanical resonance of system components such as swinging movements of a tube segment energized by e.g. a pump. Frequencies of tubing movements are given by the tubing lengths and harmonics thereof and by the beating between any frequencies involved, i.e. between different self-oscillations and pump frequencies. Mechanical fixation of the tube segments and other free components may be used to remove such mechanical resonances.

Still further, apart from the patient's heart, other physiological pulse generators in the patient may give rise to pressure pulses in the pressure signal. Generally, the physiological pulse generator may be one or more physiological phenomena such as reflexes, voluntary muscle contractions, non-voluntary muscle contractions, a heart, a breathing system, an autonomous system for blood pressure regulation and an autonomous system for body temperature regulation.

Embodiments of the invention relate to the monitoring carried out by the surveillance device 25, based on the monitoring signal. The monitoring signal may be a pressure signal as shown in FIG. 2(a), or any other time-dependent signal which is derived from the data samples output by at least one of the pressure sensors 4a-4c. This monitoring may aim at detecting one or more fault conditions in the extracorporeal circuit 20. As will be explained in the following, the detection of different fault conditions may require different types of processing for generating the monitoring signal, but generally the monitoring signal is generated to include one or more pressure pulses from the pumping device and other repetitive pulse sources in the extracorporeal circuit (collectively denoted "pump pulses" in the following). The monitoring signal may or may not also contain pulses originating from the patient (collectively denoted "physiological pulses" in the following). Common to many embodiments is that the fault detection is based on extraction of a shape measure from the monitoring signal, i.e. a measure or parameter value that represents the temporal distribution of signal values in the monitoring signal, and in particular a measure that represents the shape of a pump pulse (or a part of the pump pulse). In the context of the present application, embodiments of this fault detection are collectively referred to as "pump profile analysis".

For continuous surveillance, the pump profile analysis typically involves calculating a time sequence of values of the shape measure based on a time sequence of evaluation segments of the monitoring signal, where each evaluation segment comprises at least part of one pump pulse. The evaluation segments may be overlapping or non-overlapping in time.

In one aspect, the fault condition relates to the operation of the connection system C between the circuit 20 and the vascular system of the patient, i.e. on either the venous-side or the arterial-side, or both. One such fault condition is a disruption of the connection system C which may be caused by a dislodgement of the venous or arterial access device 1, 14 from the blood vessel access, i.e. that the access device comes loose from the vascular system of the patient. The disruption may alternatively be caused by a disconnection of the venous or arterial access device 1, 14 from the circuit 20, typically by defective coupling/uncoupling of the connectors C1a, C1b and C2a, C2b, respectively. Yet another fault condition is erroneous placement of the venous or arterial access device 1, 14 in the blood vessel access, e.g. that the access device is positioned too close to the walls of the blood vessel access such that the blood flow through the access device is blocked or obstructed, that the access device is positioned with its distal opening in the tissue of the patient causing so-called infiltration, or that the venous or arterial access devices 1, 14 have a reversed placement in the blood vessel access such that processed blood is partially re-circulated through the circuit 20 instead of re-entering the vascular system of the patient.

In another aspect, the fault condition relates to the pumping of blood through the blood pump, e.g. that there is insufficient occlusion between the pump rollers 3a, 3b and the tubing segment adapted to be engaged by the rollers (also denoted "pump segment" herein), potentially causing hemolysis of the blood.

In the following, embodiments of techniques for detecting these different fault conditions will be described under separate headings, all with reference to the exemplifying extracorporeal circuit in FIG. 1.

II. Monitoring Dislodgement/Disconnection of an Access Device

The present Assignee has surprisingly found that a dislodgement or disconnection of the arterial or venous access device 1, 14 from the blood vessel access is reflected in the shape of the monitoring signal, and specifically in the shape of the pump pulses. This surprising effect is currently believed to be caused by the fact that the shape of the pump pulses depends on pressure variations within the blood vessel access itself. The pressure variations in the blood vessel access are influenced by pressure waves that propagate into the access via the venous and the arterial access devices 1, 14, i.e. pressure waves originating from the blood pump 3, and possibly other mechanical pulse generators in the extracorporeal circuit 20. The pressure waves in the blood vessel access will in turn propagate back into the extracorporeal circuit 20 and be detected by at least one of the pressure sensors 4a-4c. A disruption of the connection system C is likely to affect the pressure variations in the blood vessel access, and thus show up as a change or deformation in the shape of the pump pulses as detected by one of the pressure sensors 4a-4c in the extracorporeal circuit 20.

In order to evaluate the shape of the pump pulses it may be preferable that the monitoring signal contains one or more pump pulses but is free, or essentially free, of physiological pulses that modify the temporal shape of the pump pulses. The lack of relevant physiological pulses may be the result of dedicated filtering of the pressure signal (e.g. in the data acquisition part 28) or may be caused by these pulses inherently being too weak to influence the measurement data obtained from the pressure sensor(s) 4a-4c. Typically, this would mean that the ratio in magnitude (e.g. peak-to-peak amplitude) between the physiological pulses and the pump pulses is less than about 1/10, preferably less than about 1/50, and most preferably less than about 1/100, as measured by the relevant pressure sensor(s) 4a-4c.

As explained by way of introduction, there are a number of known techniques for dislodgement detection based on direct or indirect monitoring of heart pulses in a pressure signal, in which an absence of a heart component in the pressure signal is taken as an indication of a dislodgement of the access device. Furthermore, WO2009/156174, which is incorporated herein by this reference, proposes improved techniques of identifying presence or absence of a heart pulse in such a pressure signal for dislodgement detection. Still further, in International patent application No. PCT/EP2010/058958, filed on Jun. 24, 2010 and incorporated herein by this reference, the present Assignee has proposed monitoring other physiological pulses in a pressure signal, such as pulses originating from the breathing system of the patient, for dislodgement detection. All of these techniques fail to operate if the physiological pulses are too weak to be detected in the pressure signal when the access devices are properly connected to the blood vessel access. The pump profile analysis used in embodiments of the invention offers an alternative or supplementary technique which is operable for dislodgement detection if and when the aforesaid techniques fail. The pump profile analysis is also operable to detect the above-mentioned disconnection of an access device from the extracorporeal circuit.

Figure 3:
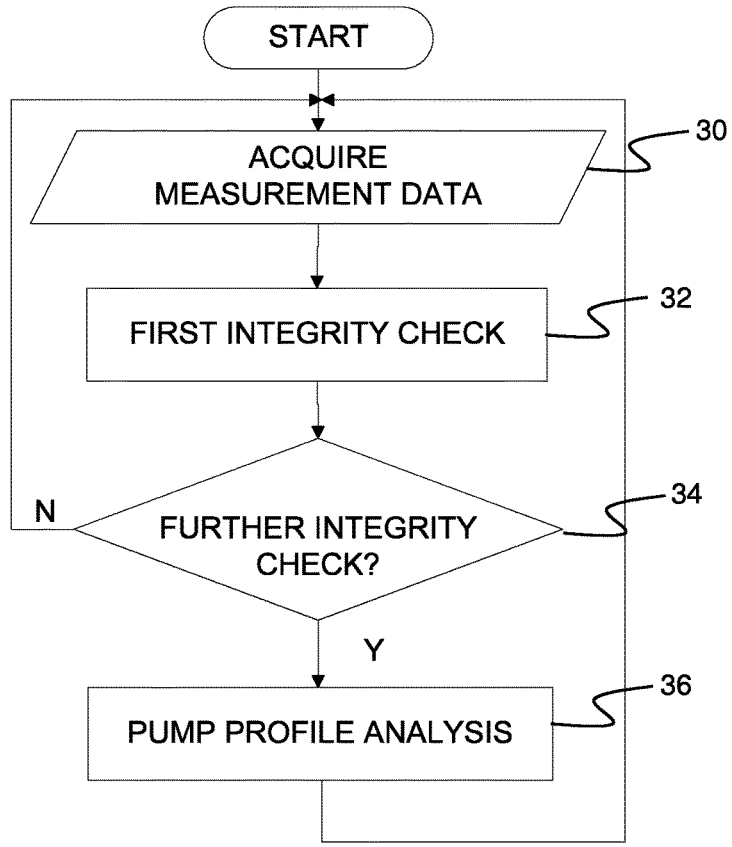
FIGS. 3-4 are flow charts of processes for monitoring fault conditions in a connection system.

FIG. 3 is a flow chart of an embodiment of a method that combines one of these known techniques ("first integrity check") with the pump profile analysis. In step 30, measurement data is acquired from one or more of the pressure sensors 4a-4c in the extracorporeal circuit 20, and in step 32 a first integrity check is performed by processing the measurement data for detection of a physiological pulse, e.g. according to any one of the aforesaid techniques. If a physiological pulse is detected, step 34 may cause the process to return to step 30. If no physiological pulse is detected, or if a need for a further integrity check is otherwise identified, step 34 may cause the process to proceed to step 36, which performs a pump pulse analysis.

Figure 4:
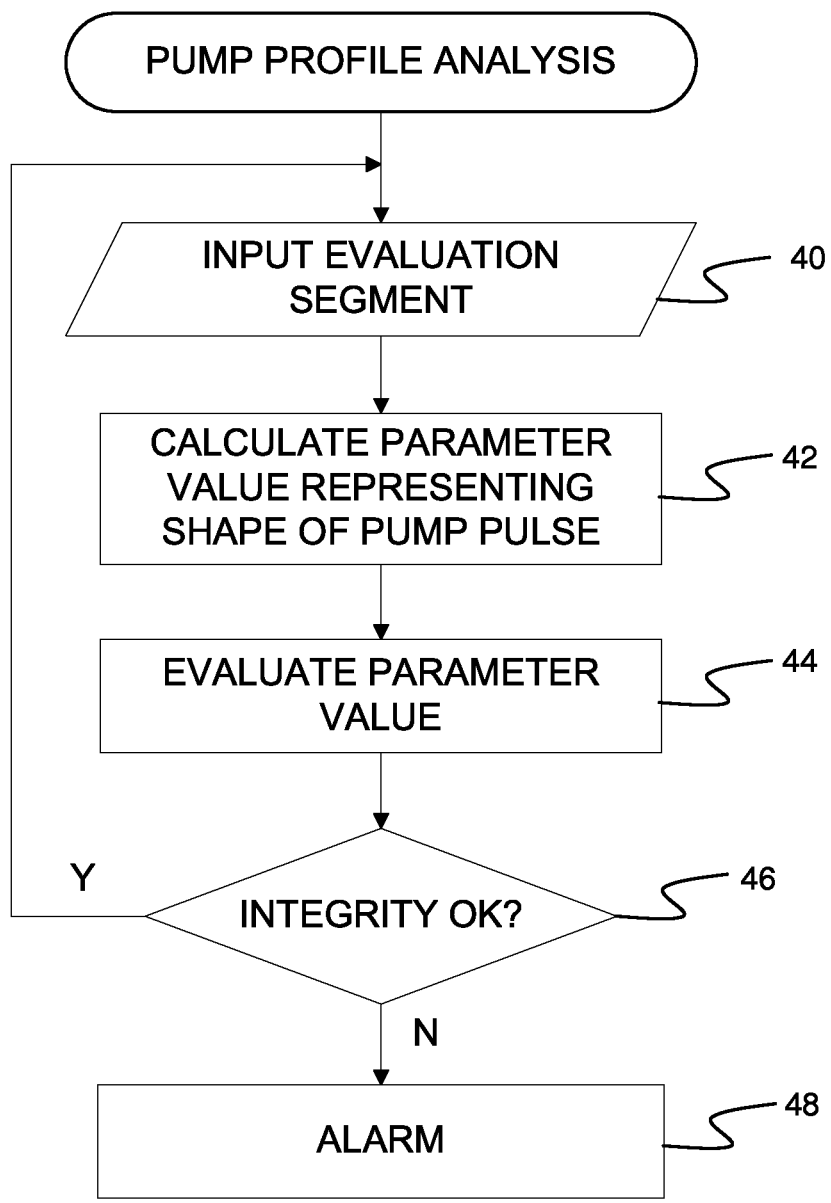

An embodiment of the pump pulse analysis is illustrated in FIG. 4. In step 40, an evaluation segment of the above-mentioned monitoring signal is generated and input. The evaluation segment may be generated based on the measurement data acquired in step 30 (FIG. 3), or based on newly acquired measurement data from the same or another pressure sensor. In step 42, the evaluation segment is processed for extraction of a parameter value that indicates the shape of the evaluation segment, and in particular the shape of the pump pulses in the evaluation segment. In step 44, the parameter value is evaluated for detection of dislodgement/disconnection. For example, the parameter value may be compared to a predetermined threshold or range. Examples of different parameter values, and techniques for their extraction, are given further below. If the evaluation of the parameter value indicates a dislodgement/disconnection, decision step 46 causes the process to proceed to step 48, in which an alarm is issued (and/or the blood flow is stopped). Otherwise, the decision step 46 causes the process to return to step 40, or alternatively to step 30 (FIG. 3).

There are many variants to the overall monitoring process shown in FIGS. 3-4. For example, steps 30-32 and steps 34-36 need not be performed in sequence for each iteration of the monitoring process. In a variant, the magnitude of the physiological pulses is evaluated, e.g. at the start of a treatment or during an intermittent stop of the pumping device(s). If the magnitude of the physiological pulses is deemed sufficient, the monitoring according to steps 32-34 may be selected for dislodgement detection; if not, the pump profile analysis of FIG. 4 may be selected for dislodgement detection. This variant may e.g. be used to improve the monitoring for dislodgement/disconnection of the venous access device 14, based on a pressure signal from the venous sensor 4c. It is not uncommon that the magnitude of the physiological pulses as measured by the pressure sensors 4a-4c, in particular heart pulses, gradually decreases during a treatment session. Thus, the first integrity check, if based on a conventional technique, may indicate a dislodgement/disconnection when the heart pulses have become too weak to be sensed by the venous sensor 4c, even if the venous access device 14 is not dislodged/disconnected. Generally, the heart pulses are stronger at the arterial sensor 4a than at the venous sensor 4c. Further, the relative magnitude of the heart pulses at the different sensors 4a-4c is relatively constant during a treatment session. The relative magnitude may be determined by comparing the heart pulses in the pressure signals of the arterial and venous sensors 4a, 4c before or during treatment, e.g. by stopping the pumping device(s) or by isolating the heart pulses by filtering the pressure signal. When the relative magnitude is known, the magnitude of the heart pulses at the venous sensor 4c may be estimated during treatment, based on the magnitude of the heart pulses in the pressure signal from the arterial sensor 4a. Thus, the monitoring process in FIG. 3 may be designed to skip the first integrity check (step 32), or at least proceed at step 34 to the pump profile analysis (step 36), whenever the pressure signal of the arterial sensor 4a indicates that the heart pulses are too weak at the venous sensor 4c.

Thus, generally, step 34 may cause the process to proceed to step 36 even if a physiological pulse is detected, e.g. whenever the monitoring process identifies a need to confirm dislodgement/disconnection (or the absence of the same) by a pump profile analysis. In yet another variant, step 34 is omitted and the integrity of the connection system is always evaluated based on the combined outcome of the first integrity check and the pump profile analysis.

In another variant, the pump profile analysis is not combined with another technique, but used on its own to detect dislodgement/disconnection.

It should be noted that the pump profile analysis may be supplemented by a filtering step before step 40, to ensure that the evaluation segments are essentially free of any potentially interfering physiological pulses. Such a filtering step may be performed in the frequency domain or the time domain, or both, using any suitable filtering technique. A specific technique for time-domain filtering is described in Section VII below.

The extraction of the parameter value in step 42 may rely on extraction of shape data from the evaluation segment. The shape data may directly or indirectly represent the temporal signal profile of the pump pulse or pulses in the evaluation segment. In one embodiment, the shape data is made up of all or a subset of the signal values in the evaluation segment, and is thus a temporal representation of the actual shape of the pump pulse(s) (denoted "temporal shape data"). The temporal shape data may or may not be a downsampled version of the evaluation segment. In one extreme, the shape data may be a subset of a pump pulse, provided that this subset is sufficiently characteristic of the pump pulse.

FIG. 5(a) illustrates temporal shape data s(n) obtained from an evaluation segment generated based on measurement data from the venous pressure sensor 4c in the extracorporeal circuit 20 of FIG. 1. In this example, the evaluation segment comprises two pump pulses P1, P2, which are generated by a respective roller in the blood pump engaging a tubing segment in the peristaltic blood pump (cf. rollers 3a and 3b in FIG. 3). FIG. 5(a) also illustrates a temporal reference profile u(n) which represents the shape of the pump pulses P1, P2 when one of the access devices is dislodged/disconnected. When the blood pump 3 is of peristaltic type, each full revolution results in two pump strokes and thus two pump pulses P1, P2. The pump strokes may result in different pump pulses, e.g. because of slight differences in the engagement between the rollers 3a, 3b and the tube segment or because of asymmetry in the mechanical design of the pump. Thus, it may be desirable for the reference profile, and thus the evaluation segment, to include both pump pulses P1, P2.

FIG. 5(b) illustrates a temporal shape data s(n) obtained from an evaluation segment generated based on measurement data from the arterial pressure sensor 4a in the extracorporeal circuit 20 of FIG. 1, and a corresponding temporal reference profile u(n).

In another embodiment, the shape data is made up of spectral shape data, such as signal amplitude given as a function of frequency and/or signal phase given as a function of frequency. Such spectral shape data (denoted "spectral shape data") may be obtained by spectral analysis of the evaluation segment, e.g. via Fourier analysis or any equivalent technique. It should be noted that a complete representation of the shape of the evaluation segment would require the spectral shape data to include both the frequency distribution in amplitude and the frequency distribution in phase. In the context of the present application, however, either one of these frequency distributions is deemed to represent the shape of the evaluation segment and may thus be used to calculate the parameter value, by comparing the frequency distribution to a corresponding reference profile, which is given as a frequency distribution of signal amplitude or phase, as applicable (cf. FIGS. 15(a)-15(d) below).

The parameter value may represent the similarity or dissimilarity between the temporal or spectral shape data and one or more reference profiles. The parameter value may thus be derived by comparing or matching the shape data to the reference profile(s).

If two reference profiles are used, one may represent an intact connection system and one may represent a compromised connection system. The comparing/matching may thus result in two parameter values, which may be evaluated collectively to determine the integrity of the connection system.

Although the following description assumes that only one reference profile is used, it is equally applicable to the use of two reference profiles.

In one embodiment, using temporal shape data, the parameter value is obtained by convolving or cross-correlating the temporal shape data s(n) and the temporal reference profile u(n), with the parameter value being given by a resulting correlation value, typically the maximum correlation value.

Figure 5:
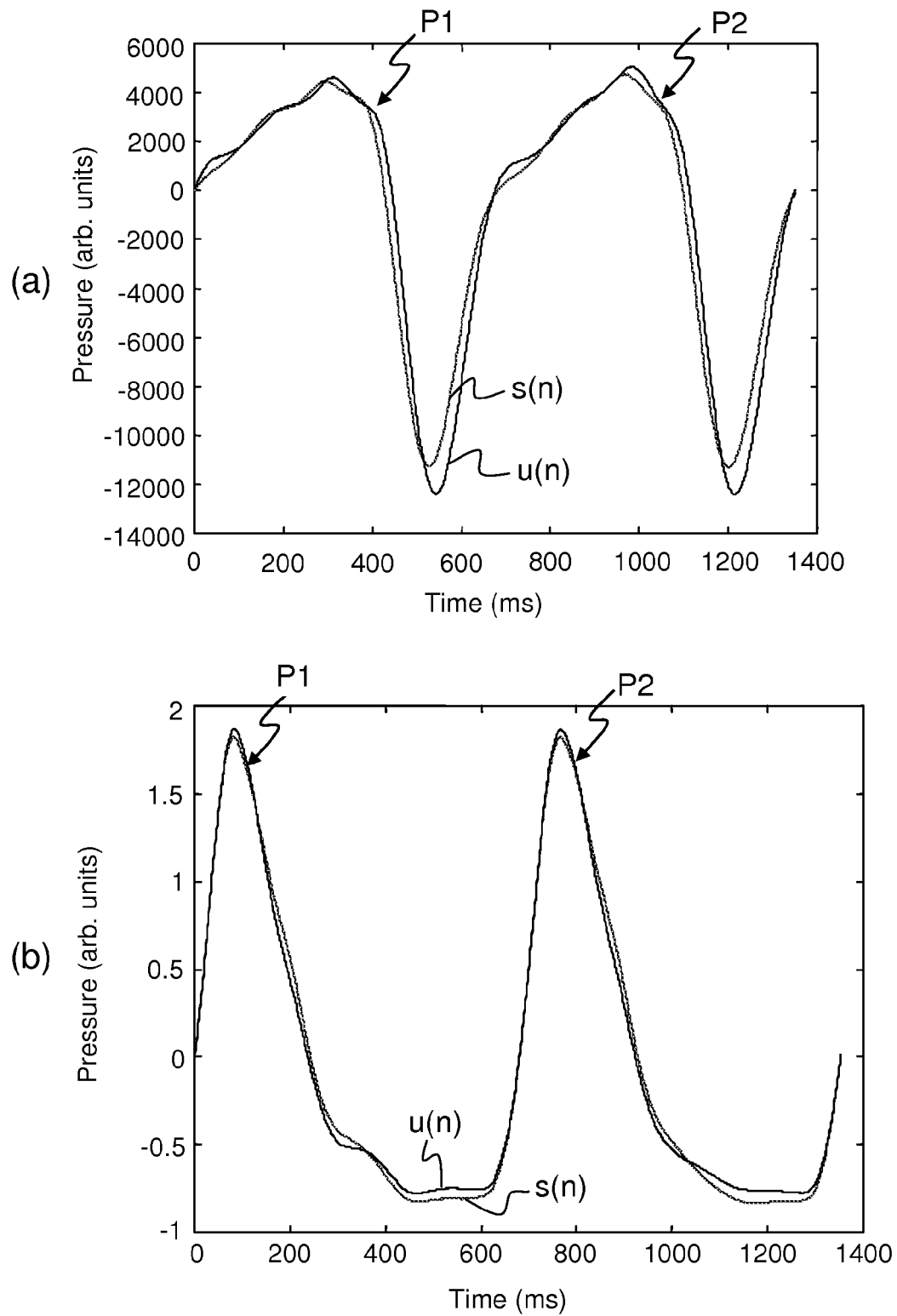
FIGS. 5($a$)-5($b$) are plots of a reference profile and an actual profile of pump pulses, acquired from a venous pressure sensor and an arterial pressure sensor, respectively.

In another embodiment, using temporal shape data, the temporal shape data s(n) and the temporal reference profile u(n) are aligned with each other, such that the pump pulse(s) in the shape data and the reference profile overlap (e.g. as shown in FIG. 5), based on pump timing information which indicates the timing of the pump pulse(s) in the temporal shape data s(n). The pump timing information may be obtained from the pump sensor 26 or the control unit 23 (see FIG. 1). Alternatively, the pump timing information may be calculated from a pressure signal obtained from one of the pressure sensors in the circuit. Such pump timing information may alternatively be implicit, e.g. if each evaluation segment is generated with known timing with respect to the pump pulses. In such a variant, the temporal shape data may be extracted and directly aligned with the temporal reference profile.

In an embodiment using the above-mentioned spectral shape data, spectral shape data may be directly aligned with a corresponding reference profile, since both the spectral shape data and the reference profile may be given within a known range of frequencies.

The comparing/matching process may or may not include an "autoscaling" between the shape data and reference profile, in which the magnitude of one is adapted to the magnitude of the other, e.g. by minimizing a measure of the difference between the shape data and the reference profile, as is well-known in the art. The autoscaling may improve the robustness of the monitoring process, e.g. by reducing the influence of disturbances affecting the magnitude of the pump pulses in the measurement data. On the other hand, in certain situations, autoscaling may be avoided since it discards magnitude information which may be useful for detecting a dislodgement/disconnection.

The parameter value may be calculated as a correlation value, a sum of differences between mutually aligned signal values in the shape data and the reference profile, or any suitable $L^n$-norm evaluated based on these differences, such as an $L^1$-norm (sum of absolute differences, aka Manhattan norm) or an $L^2$-norm (Euclidian norm). In any such calculations, the shape data and/or the reference profile may be weighted by a suitable function, e.g. to reduce the impact on the parameter value of certain parts of the shape data. The skilled person realizes that any known difference/similarity measure may in fact be evaluated and used as parameter value indicative of the shape of the pump pulse(s).

It should be understood, though, that the temporal shape data may include a larger number of pump pulses than the reference profile, whereby each temporal shape data may be matched against several reference profiles, which may or may not be identical. For example, when the blood pump has a number of different pump strokes, each generating a unique pump profile (cf. P1, P2 in FIG. 5), the temporal shape data may be matched against a set of reference profiles representing the different pump profiles.

The above-described embodiments rely on the use of a reference profile (temporal or spectral) that properly represents the temporal profile of the pump pulse(s). It should be understood that the reference profile may represent either an intact connection system, in which the access devices are properly arranged in the blood vessel access, or a compromised connection system, in which one of the access devices is dislodged/disconnected. For example, the reference profile may be obtained in a reference measurement, based on measurement data acquired from one or more of the pressure sensors 4a-4c in the circuit 20, suitably by identifying and possibly averaging a set of pump pulses in the measurement data. During the reference measurement, the physiological pulses are either prevented from reaching the relevant pressure sensor, or they are removed in a filtering step similarly to the above-mentioned filtering step preceding step 40 in FIG. 4. In another variant, the reference measurement may operate on measurement data from a pressure sensor which is substantially isolated from the physiological pulses. In such a situation, the reference profile may be obtained from the isolated sensor, and used for generating the reference profile (optionally after adjustment/modification for differences in confounding factors, see below), which is then used in the actual monitoring process. For example, the pressure signal from the system sensor 4b in the extracorporeal circuit 20 of FIG. 1 may be essentially isolated from the physiological pulses, and this pressure signal may thus be used in a reference measurement, while the actual monitoring process may operate on measurement data from either of the pressure sensors 4a-4c.

If the reference profile represents an intact connection system, the reference measurement may be carried out before treatment but after connection of the access devices to the blood vessel access (e.g. during priming) or during treatment (i.e. during blood processing), or in simulated environment with blood or any other fluid. If the reference profile represents a compromised connection system, the reference measurement may be carried out during a simulated dislodgement of one of the access devices, preferably in a simulated environment, or during priming (e.g. at the end of priming when the arterial access device 1 is connected to the blood vessel access and the venous access device 14 is not). Alternatively, a predetermined (i.e. predefined) reference profile may be used, which optionally may be modified according to a mathematical model accounting for wear in the blood pump, blood flow rates, tubing dimensions, speed of sound in the blood, etc.

Different embodiments for predicting or estimating the reference profile (temporal or spectral) in the extracorporeal circuit 20 of FIG. 1 are further described in the Section VI: "Obtaining a reference profile of pump pulses" further below.

Above, it was stated that the monitoring signal preferably is essentially free of physiological pulses. It is likely that the timing, and possibly also the shape, of the physiological pulses will vary during a blood treatment. If the pump profile analysis is to be performed in the presence of one or more physiological pulses in the monitoring signal, the shape and timing of the physiological pulses should be known or at least predictable.

Under these circumstances, the physiological pulse(s) may be part of/added to the reference data, and thus the pump profile analysis may be executed according to any of the above embodiments/examples.

Figure 6:
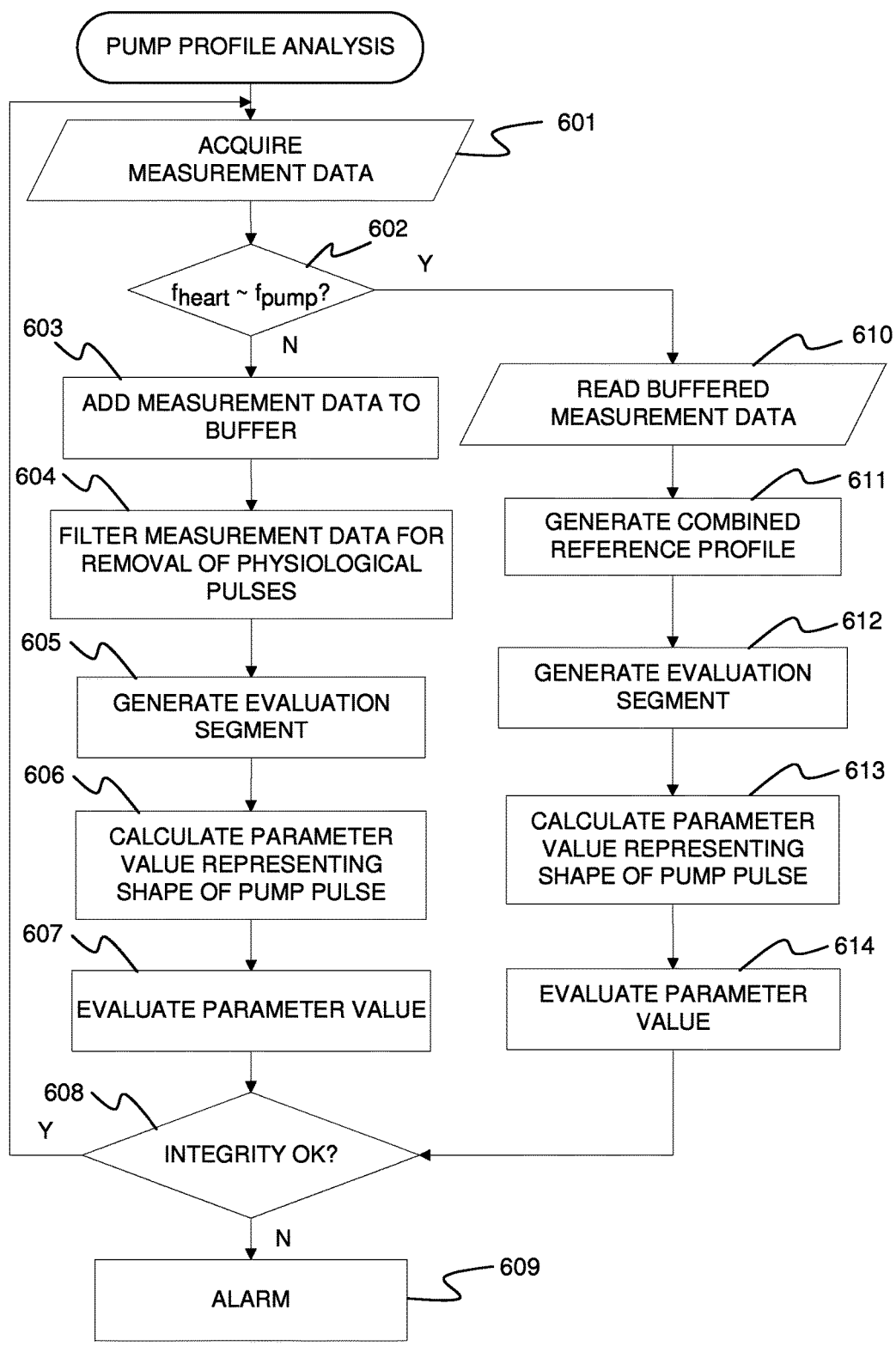
FIG. 6 is a flow chart of a process for monitoring fault conditions in a connection system.

FIG. 6 is a flowchart of a variant of the monitoring process designed to address a situation that is troublesome for most dislodgement detection techniques, namely when the frequency of the physiological pulses, specifically the heart pulses, essentially coincides with one of the frequency components of the pump pulses (cf. $0.5f_0$, $f_0$, $1.5 f_0$, etc in FIG. 2(b)). In step 601, measurement data is acquired from a pressure sensor like in the foregoing embodiments. In step 602, it is checked if there is an overlap between a physiological pulse and a pump pulse in the frequency domain. Typically, it is checked if a frequency component of the physiological pulse(s) falls within a confined range around any significant frequency component of the pump pulses. If no such overlap is detected, the process proceeds to step 603, in which the measurement data is added to a buffer in a memory unit of the surveillance device. Step 603 is followed by steps 604-609 which correspond to steps 40-48 in FIG. 4 and which will not be repeated here. If an overlap is detected in step 602, the process proceeds to step 610, in which measurement data is read from the buffer. Typically, the buffer stores measurement data acquired during a limited number of preceding iterations of the monitoring process. In step 611, the buffered measurement data is processed to generate a reference profile containing both one or more pump pulses and one or more physiological pulses. Since the buffered measurement data is acquired during the last few immediately preceding iterations, it may be presumed that both the pump pulses and the heart pulses are adequately reproduced in the reference profile. The process then proceeds with steps 612-614 which correspond to steps 40-44 in FIG. 4 and which will not be repeated here.

III. Monitoring Relative Location of Access Devices

Figure 7:
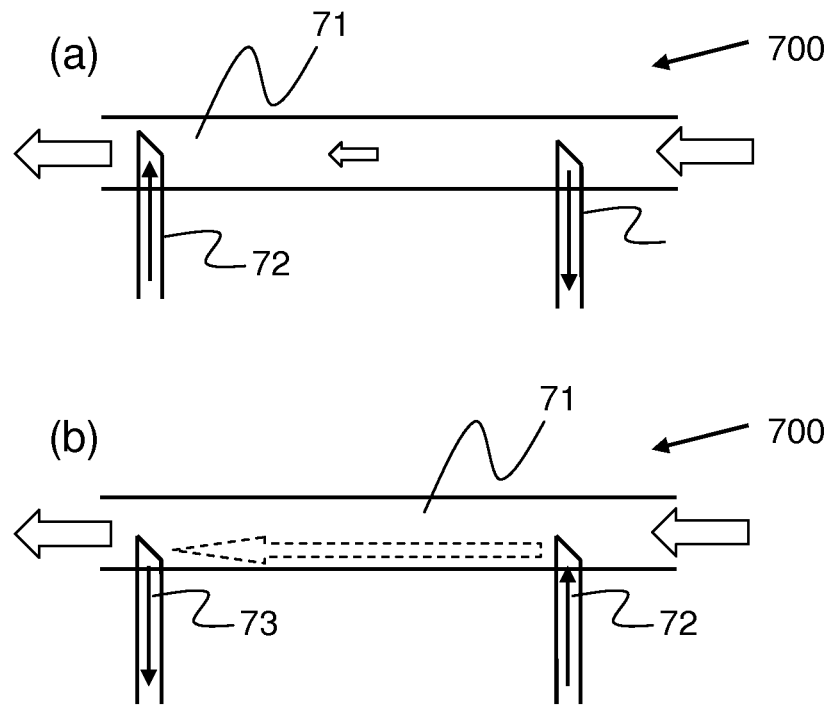
FIG. 7($a$) is a view of access devices in a normal configuration at an access site, and FIG. 7($b$) is a view of the corresponding access site with the access devices in a reversed configuration.

FIG. 7 illustrates an access site with a blood vessel access 71 and access devices 72, 73 in a normal configuration (FIG. 7(a)) and a reversed configuration (FIG. 7(b)), where the access devices 72, 73 correspond to access devices 14, 1 in FIG. 1. The blood flows in the blood vessel access and the access devices are indicated by arrows. In normal configuration, the arterial access device 73 is positioned upstream for extracting blood and the venous access device 72 is positioned downstream for returning blood to the blood vessel access 71. In reversed configuration, the arterial access device 73 is positioned downstream and the venous access device 72 upstream, with the consequence of treated blood being returned upstream and being extracted downstream by the arterial access device 73. In the reversed configuration, some of the blood is withdrawn and re-dialyzed without being passed through the vascular system of the patient, with significantly reduced treatment efficiency as a consequence. It should be noted that a reversed configuration may occur either as a result of a reversed placement of the access devices 72, 73 in the blood vessel access 71, or as a result of a reversed coupling of the connectors C1b, C2b to the connectors C1a, C2a.

Figure 8:
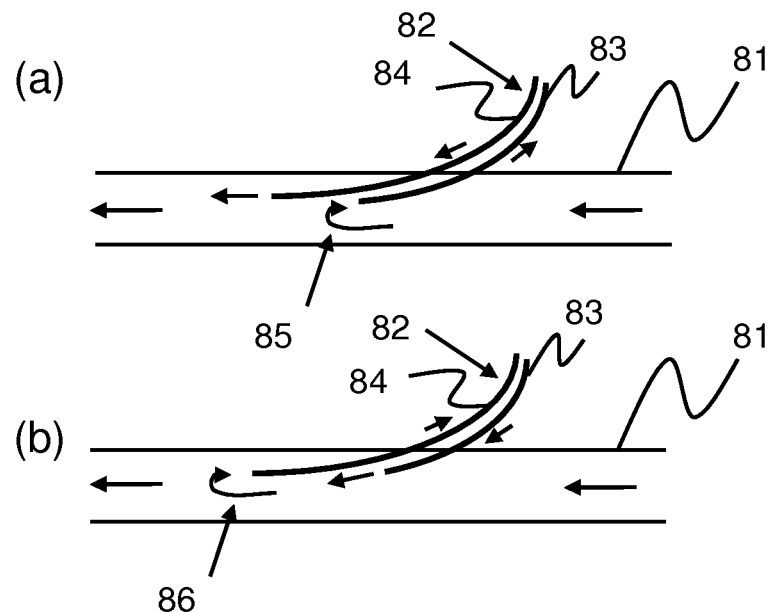
FIG. 8($a$) is a view of withdrawal and return lines of a double lumen needle or catheter in a normal configuration at an access site, and FIG. 8($b$) is a view of the corresponding access site with the withdrawal and return lines in a reversed configuration.

In extracorporeal blood treatments, two needles are commonly used to puncture the skin to gain access to the patient's blood supply. The arterial needle removes the blood, and the venous needle is used to return the treated blood to the patient. Alternatively, a double lumen catheter may be used as shown in FIG. 8. A double lumen catheter comprises two parallel channels which terminate at a distance from each other. One lumen removes the blood, and the other lumen is used to return the treated blood to the patient. FIG. 8 shows an access site with a blood vessel access 81 and a double lumen needle 82 inserted and having an arterial lumen 83 and a venous lumen 84. FIG. 8(a) illustrates a normal situation with the withdrawal and return blood lines (not shown) connected such that the arterial lumen 83 is withdrawing blood (indicated by 85), and the venous lumen 84 is returning blood. Flow directions are indicated with arrows. FIG. 8(b) illustrates a situation with a reversed connection of the blood lines to the respective lumen, such that the venous lumen 84 withdraws blood and the arterial lumen 83 returns blood, resulting in recirculation since the arterial lumen 83 is upstream in relation to the venous lumen 84 (indicated by 86). Another type of malfunction may occur if the double lumen catheter is inserted in a reversed direction into a blood vessel, such that the inlet and outlet of the double lumen catheter are reversed with respect to the flow in the blood vessel.

The reversed configuration is a fault condition in the connection system, and it has been found to cause changes in the shape of the pump profiles as recorded by pressure sensors in the extracorporeal circuit. Thus, the embodiments for monitoring dislodgement/disconnection (Section II) are equally applicable for monitoring the relative location of the access devices.

To give a few examples, it has been deemed possible to detect a reversed configuration by matching temporal or spectral shape data obtained from an evaluation segment against a reference profile.

In a variant, the reversed configuration may be detected by comparing shape features in different parts of a pump pulse to each other. For example, a parameter value may be formed by the ratio between magnitudes (e.g. amplitude, integrated area, etc) of first and second local maxima in the pump pulse. Other parameter values may be formed by the magnitude of a local maximum, by a rate of change (e.g. rise time, fall time, slope, etc) on a first side, second side or both sides of a local maximum in the pump pulse, by a width of the pump pulse at a predetermined distance from a local maximum in the pump pulse, etc.

In a further variant, the reversed configuration is detected by comparing shape features obtained from plural monitoring signals, each originating from a different pressure sensor in the extracorporeal circuit. For example, one monitoring signal may be generated based on the pressure signal from the arterial pressure sensor (4a in FIG. 1) and one monitoring signal may be generated based on the pressure signal from the venous pressure sensor (4c in FIG. 1). Typically, the shape features are obtained from corresponding pump pulses in the monitoring signal, i.e. pump pulses that have a common origin. For example, the parameter value may be formed by the ratio between the magnitudes of the pump pulses, or the ratio between the magnitudes of a selected segment in the pump pulses.

IV. Monitoring Positioning of Access Device

For proper operation of the extracorporeal circuit 20 and the blood treatment process, it is also important to ensure that each access device 1, 14 is properly installed in the blood vessel access. The installation of the access device is a manual operation that requires skill and experience of the operator. Human errors are not uncommon in this context. For example, the distal end of the access device 1, 14 may be inserted too far into the blood vessel access, causing the blood flow through the access device to be blocked/obstructed by the wall of the access. Alternatively, the distal end of the access device may be positioned in the tissue of the patient causing so-called infiltration.

These types of fault conditions in the connection system between the extracorporeal circuit and the vascular system of the patient have been found to cause changes to the shape of the pump profiles as recorded by pressure sensors in the extracorporeal circuit. Thus, the embodiments for monitoring dislodgement/disconnection (Section II) are equally applicable for monitoring the positioning of the access devices.

V. Monitoring Condition of Blood Pump

The present Assignee has also realized that the blood pump 3 may be diagnosed based on measurement data obtained from one or more pressure sensors in the extracorporeal circuit 20, either before or during blood treatment.

Specifically, different fault conditions of the blood pump 3 may be identified based on the pump profiles in the aforesaid monitoring signal. Thus, the embodiments for monitoring dislodgement/disconnection (Section II) are equally applicable for monitoring the condition of the blood pump.

It may be important to diagnose the blood pump during or between blood treatments, since fault conditions in the blood pump may not only reduce the expected life of the pump, but may also cause life-threatening conditions of the patient. One life-threatening condition may originate from insufficient occlusion between the pump rollers 3a, 3b and the tubing segment during rotation of the rotor 3 (FIG. 1), if the insufficient occlusion generates shear forces in the blood that cause hemolysis of the blood which is then circulated back to the patient. Further fault conditions are discussed in more detail below.

Figure 9:
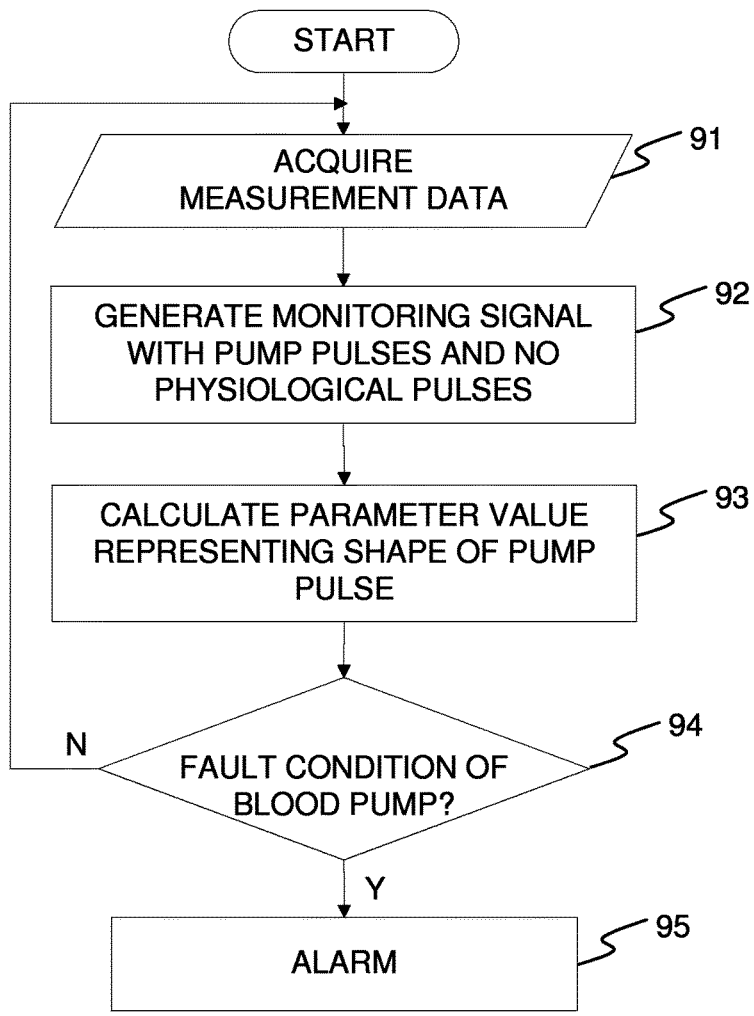
FIG. 9 is a flow chart of a process for monitoring fault conditions in a blood pump.

FIG. 9 is a flow chart of an embodiment of a process for detecting a fault condition in the blood pump. In step 91, measurement data is acquired from one or more of the pressure sensors 4a-4c in the extracorporeal circuit 20, and in step 92 the measurement data is processed to generate a time-dependent monitoring signal which contains one or more pump pulses and no physiological pulses. Step 92 may involve filtering the measurement data to remove physiological pulses, and possibly unwanted mechanical pulses from the extracorporeal system, such that the monitoring signal only contains the pressure pulses of interest. For example, the time-domain filtering described in Section VII may be used. Alternatively or additionally, step 92 may be executed while the extracorporeal circuit 20 is disconnected from the patient (e.g. by detaching one of the access device 1, 14 from the circuit 20 or from the blood vessel access), or the physiological pulses are otherwise prevented from reaching the relevant pressure sensor (e.g. while the physiological pulses are to weak to be detected by the venous sensor 4c or the system sensor 4b). In step 93, a shape-indicative parameter value is calculated, e.g. as described above in Section II. In step 94, the parameter value is evaluated to identify one or more fault conditions of the blood pump. If a fault condition is detected, an alarm is issued (step 95), and the blood pump is possibly shut down. If proper pump operation is determined, the process returns to step 91.

The following fault conditions may be identified based on the shape of the pump profiles.

Figure 10:
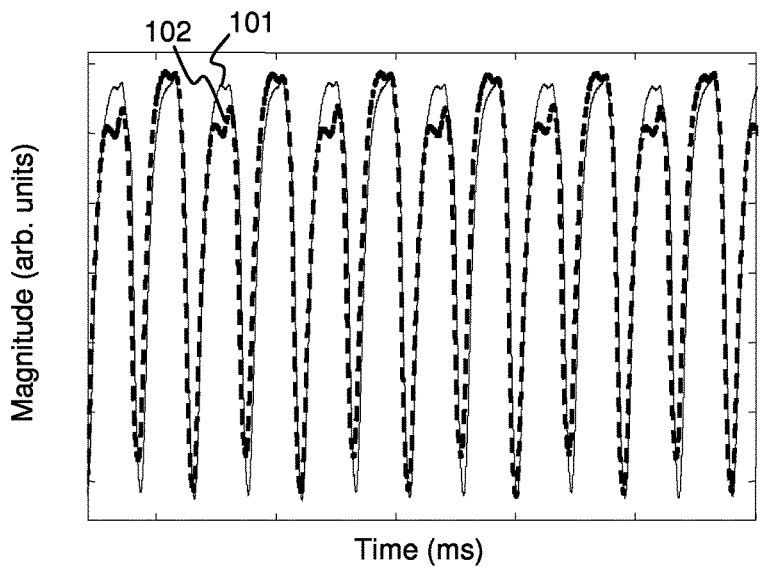
FIG. 10 is a plot of pump pulses in the time domain for a poorly calibrated and a well-calibrated blood pump FIG. 11($a$) is a frequency spectrum of pump pulses for the poorly calibrated pump, and FIG. 11($b$) is a frequency spectrum of pump pulses for the well-calibrated pump.
Figure 11:
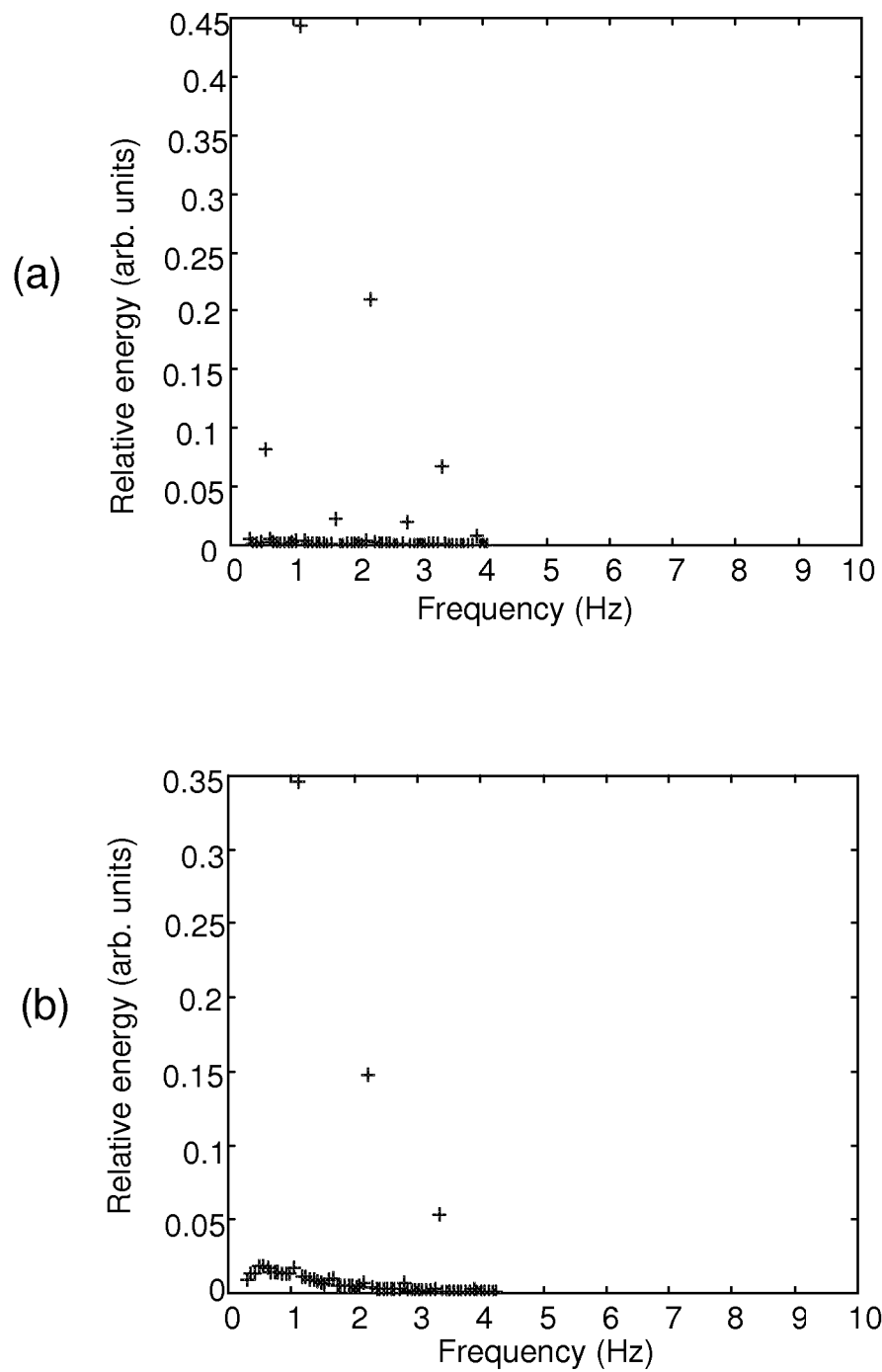

1. Mechanical Irregularities of Pump
   a. Incorrect Calibration of Pump
      FIG. 10 shows a monitoring signal 101 with pump pulses originating from a correctly adjusted pump, and a monitoring signal 102 with pump pulses originating from an incorrectly adjusted pump. In the illustrated example, the pulses are detected by the venous pressure sensor 4a with the blood pump 3 operating at a flow rate of 300 ml/min. The blood pump 3 was adjusted incorrectly by the rollers (cf. 3a, 3b in FIG. 1) being positioned with too large gaps to the supporting track of the pump body causing lack of occlusion. Clearly the time-domain pump pulses differ between the monitoring signals 101, 102. The deviating shape in the monitoring signal may be detected indirectly by calculating the parameter value as a dispersion measure based on the signal values in the monitoring signal, or a subset thereof (such as the envelope of the monitoring signal, e.g. given by the local maxima and/or minima). Alternatively, the parameter value may be calculated to represent the symmetry between consecutive pump pulses in the monitoring signal, i.e. the pump pulses originating from the action of the different pump rollers. Still further, the parameter value may be calculated by a step of comparing/matching temporal/spectral shape data to one or more reference profiles, as described in Section II. Lack of symmetry may be used as an indicator of poor calibration. The lack of calibration may alternatively be detected in the frequency domain, as indicated by the energy spectral density plots of FIGS. 11(a) and 11(b). In FIG. 11(a), an unbalance between the two rollers 3a, 3b causes higher amplitudes of the frequencies corresponding to (full turn) harmonics of the revolution speed of the pump compared to the case with correctly adjusted rollers (FIG. 11(b)).

b. Unbalanced Pump Shaft or Pump Head
      If the pump shaft is not aligned with the axis for correct performance of the peristaltic pump, it may cause concentric variations of the gap between the rollers and the pump body over each revolution of the pump. This will result in an unbalanced set of pump pulses which may be detected in a similar way as in 1a. Note that the pressure variation due to poor occlusion may differ between case 1a and 1b.

2. User Handling Fault
   a. Incorrect Pump Segment
      This fault condition may be detected by comparing the actual pump pulses detected by the venous and/or arterial sensors 4a, 4c to the predicted pump pulses of a given type of pump segment. If e.g. a too small pump segment has been mounted on the peristaltic pump by mistake, the actual pump pressure profiles would deviate from the expected as if both pump rollers were incorrectly calibrated with too large gaps to the pump body.

b. Other Types of Handling Faults
      It may be anticipated that other types of handling faults may cause similar deviation of the pump pulses, e.g. after incorrect mounting of pump segment (twisted, stretched pump segment, wrong position).

VI. Obtaining a Reference Profile of Pump Pulses

Generally, the reference profile is dependent on the operational state of the extracorporeal circuit 20. For example, if the rotation frequency of the blood pump 3 is changed, e.g. to change the blood flow rate through the circuit, the shape of the pump profile(s) will change. This effect can be addressed in different ways.

In a first embodiment, a reference measurement is carried out intermittently during treatment, so as to derive an updated reference profile to be used in the monitoring process until the next reference measurement. The reference measurement may be triggered by a change in the operational state of the circuit, or be carried out at regular time intervals.

Figure 12:
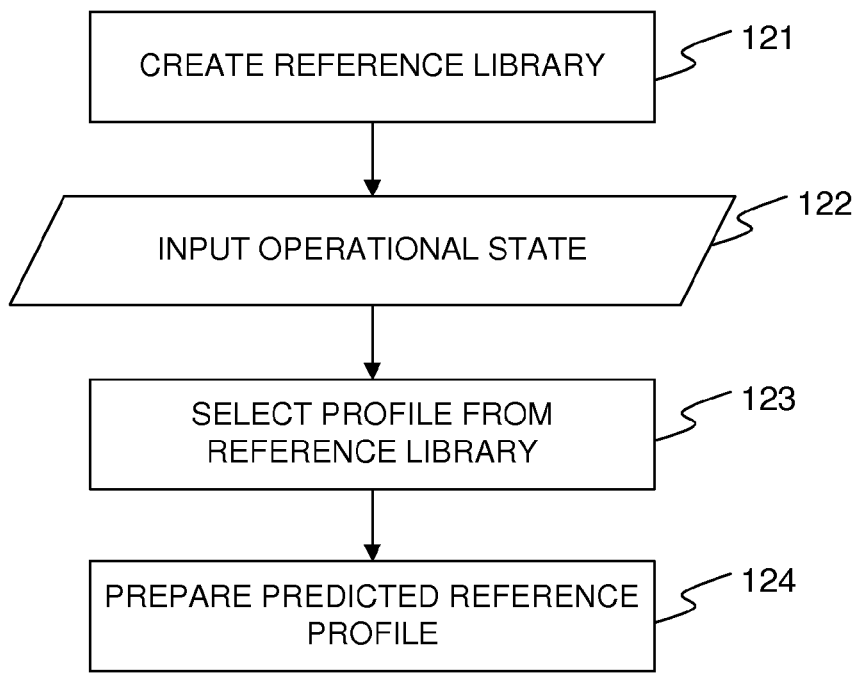
FIG. 12 is a flow chart of a process for obtaining a predicted reference profile.

FIG. 12 is a flow chart of a second embodiment. In the second embodiment, a reference library or database is first created based on the reference measurement (step 121). The resulting reference library is typically stored in a memory unit, e.g. RAM, ROM, EPROM, HDD, Flash, etc, in the surveillance device 25. During the reference measurement, reference profiles (temporal or spectral) are acquired for a number of different operational states of the extracorporeal circuit 20. Each operational state is represented by a unique combination of system parameter values. For each operational state, a reference profile is generated to represent the temporal signal profile of the pump pulses. The reference profiles together with associated system parameter values are then stored in the reference library, which is implemented as a searchable data structure, such as a list, look-up table, search tree, etc. In the following, the profiles stored in the library are denoted "library profiles" to distinguish them from the reference profiles used in calculating the parameter value during the actual monitoring process.

During the actual monitoring process, current state information indicating the current operational state of the extracorporeal circuit is obtained from the system, e.g. from the pump sensor 26, the control unit 23 or otherwise (step 122). The current state information may include a current value of one or more system parameters. The current value is then matched against the system parameter values in the reference library. Based on the matching, one or more library profiles are selected (step 123) and used for preparing a predicted reference profile (step 124) for use in the monitoring process.

Generally, the aforesaid system parameters represent the overall system state, including but not limited to the structure, settings, status and variables of the extracorporeal circuit or its components. In the system of FIG. 1, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4c), arterial pressure (from sensor 4a) and system pressure (from sensor 4b), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the extracorporeal circuit during the monitoring process. In other words, the pump frequency is used as search variable in the reference library. The pump frequency may e.g. be given by a set value for the blood flow rate output from the control unit 23, or by an output signal of the pump sensor 26. Alternatively, the pump frequency may be obtained by frequency analysis of the pressure signal from any of the sensors 4a-4c during operation of the fluid system. Such frequency analysis may be achieved by applying any form of harmonics analysis to the pressure signal, such as Fourier or wavelet analysis. As indicated in FIG. 2(*b*), the base frequency $f_0$ of the pump may be identified in a resulting power spectrum.

In the following, three examples are given of techniques for generating a predicted reference profile by accessing such a reference library.

Figure 13:
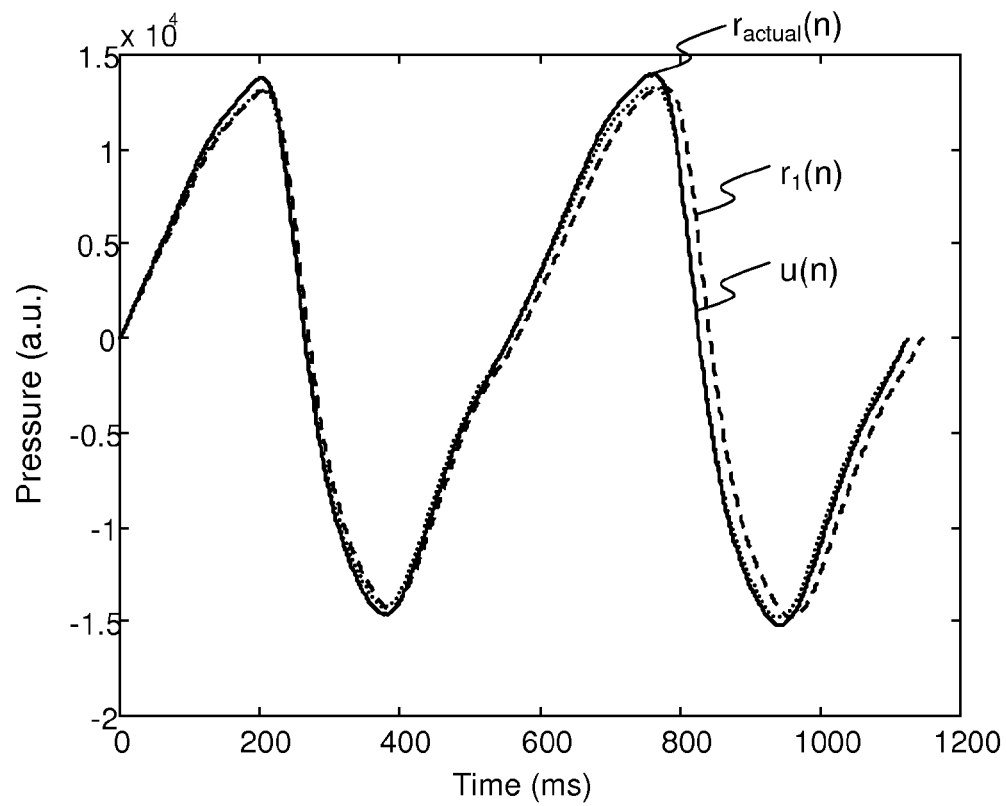
FIG. 13 is a plot to illustrate an extrapolation process for generating a predicted reference profile.

In a first example, the library profiles stored in the reference library are temporal profiles. The reference library is searched for retrieval of the library profile that is associated with the pump frequency that lies closest to the current pump frequency. If no exact match is found to the current pump frequency, an extrapolation process is executed to generate the predicted reference profile. In the extrapolation process, the retrieved library profile is scaled in time to the current pump cycle, based on the known difference ("pump frequency difference") between the current pump frequency and the pump frequency associated with the retrieved library profile. The amplitude scale may also be adjusted to compensate for amplitude changes due to pump frequency, e.g. based on a known function of amplitude as a function of pump frequency. FIG. 13 illustrates a library profile $r_1(n)$ obtained at a flow rate of 470 ml/min, and a predicted reference profile $u(n)$ which is obtained by scaling the library profile to a flow rate of 480 ml/min. For comparison only, a reference profile $r_{actual}(n)$ obtained at 480 ml/min is also shown, to illustrate that extrapolation process indeed may yield a properly predicted reference profile.

In a second example, the library profiles stored in the reference library are temporal profiles. The reference library is again searched based on current pump frequency. If no exact match is found to the current pump frequency, a combination process is executed to generate the predicted reference profile. Here, the library profiles associated with the two closest matching pump frequencies are retrieved and combined. The combination may be done by re-scaling the pump cycle time of the retrieved library profiles to the current pump frequency and by calculating the predicted reference profile via interpolation of the re-scaled library profiles. For example, the predicted reference profile $u(n)$ at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved library profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted reference profile $u(n)$ may be generated by combining more than two library profiles.

Figure 14A:
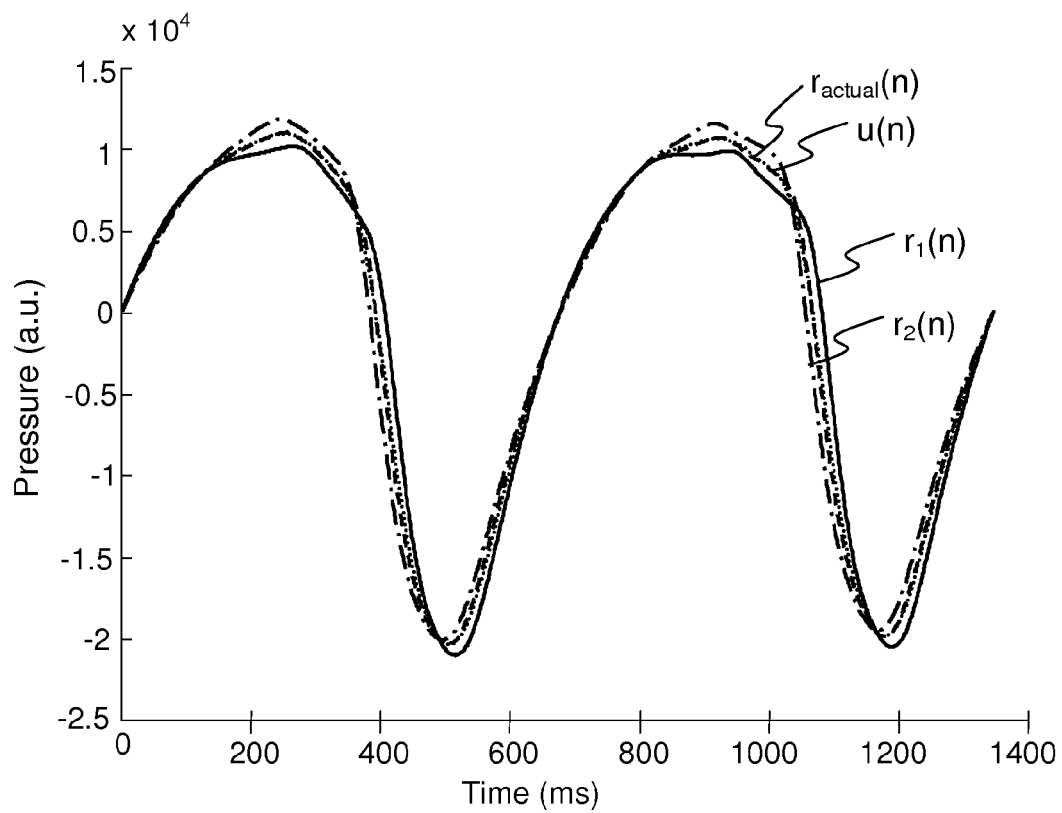
FIG. 14($a$) is a plot to illustrate an interpolation process for generating a predicted reference profile, and FIG. 14($b$) is an enlarged view of FIG. 14($a$).
Figure 14B:
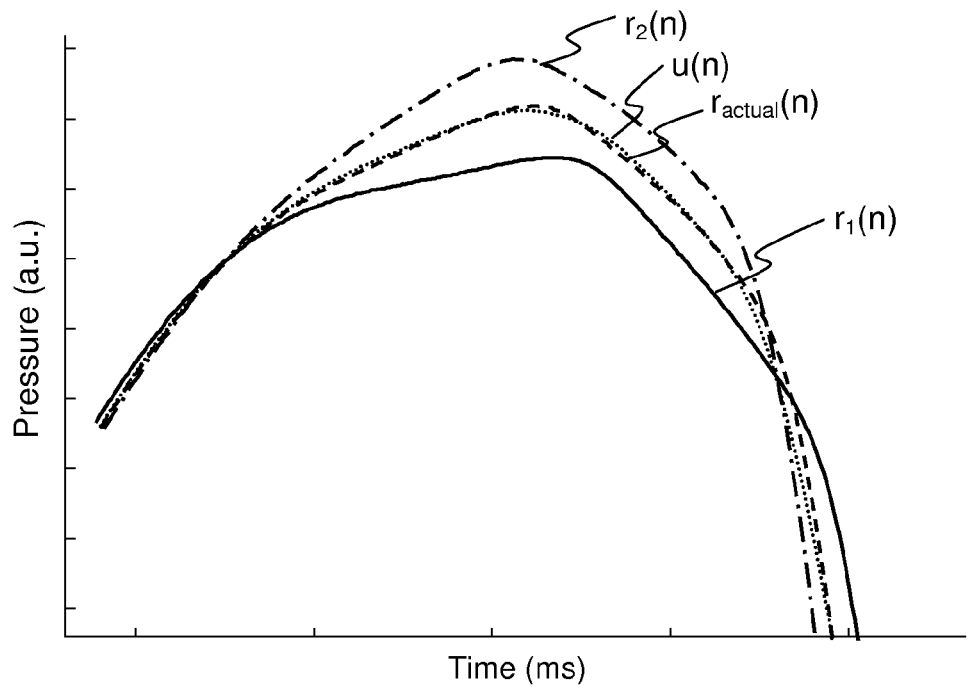

FIG. 14(*a*) illustrates a predicted reference profile $u(n)$ at a current flow rate of 320 ml/min for measurement data obtained from the venous sensor 4c in the system of FIG. 1. The predicted reference profile $u(n)$ has been calculated as an average of a library profile $r_1(n)$ obtained at a flow rate of 300 ml/min from the venous sensor and a library profile $r_2(n)$ obtained at a flow rate of 340 ml/min from the venous sensor. For comparison only, a reference profile $r_{actual}$) obtained at 320 ml/min is also shown, to illustrate that the combination process indeed may yield a properly predicted reference profile. In fact, the differences are so small that they are only barely visible in the enlarged view of FIG. 14(*b*).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 12, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data (i.e. spectral profiles) are then stored in a reference library together with the associated system parameter values (cf. step 121 in FIG. 12). The implementation of the reference library may be the same as in the second embodiment.

During the actual monitoring process, a current value of one or more system parameters is obtained from the extracorporeal circuit (cf. step 122 in FIG. 12). The current value is then matched against the system parameter values in the reference library. Based on the matching, a specific set of energy and phase data may be retrieved from the reference library to be used for generating the predicted reference profile (cf. step 123 in FIG. 12). The predicted reference profile may be temporal and may be generated by adding sinusoids of appropriate frequency, amplitude and phase, according to the retrieved energy and phase data (cf. step 124 in FIG. 12). Alternatively, the predicted reference profile may be spectral, for matching against spectra shape data.

Generally speaking, without limiting the present disclosure, it may be advantageous to generate a predicted temporal reference profile from energy and phase data when the pump pulses (to be analysed in the monitoring process) is expected to contain only one or a few base frequencies (and harmonics thereof), since the predicted temporal reference profile may be represented by a small data set (containing energy and phase data for the base frequencies and the harmonics). On the other hand, when the power spectrum of the pump pulses is expected to be more complex, e.g. a mixture of many base frequencies, it may instead be preferable to generate the predicted temporal reference profile from one or more library profiles.

FIG. 15(*a*) represents an energy spectrum of a reference signal acquired at a flow rate of 300 ml/min in the system of FIG. 1. In this example, the reference signal essentially consists of a basic pump frequency at 1.2 Hz ($f_0$, first harmonic) and a set of overtones of this frequency (second and further harmonics). Compared to the power spectrum of FIG. 2(*b*), the pressure signals used for generating the graphs in FIG. 15(*a*)-15(*d*) do not contain any significant frequency component at $0.5f_0$ and its harmonics. The graph in FIG. 15(*a*) displays the relative energy distribution, wherein the energy values have been normalized to the total energy for frequencies in the range of 0-10 Hz. FIG. 15(*b*) represents energy spectra of reference signals acquired at three different flow rates in the system of FIG. 1. The energy spectra are given in logarithmic scale versus harmonic number (first, second, etc). As shown, an approximate linear relationship may be identified between the logarithmic energy and harmonic number for the first four to five harmonic numbers. This indicates that each energy spectrum may be represented by a respective exponential function. FIG. 15(*c*) illustrates the data of FIG. 15(*b*) in linear scale, wherein a respective polynomial function has been fitted to the data. As indicated in FIGS. 15(*a*)-15(*c*), the energy spectra may be represented in different formats in the reference library, e.g. as a set of energy values associated with discrete frequency values or harmonic numbers, or as an energy function representing energy versus frequency/harmonic number.

FIG. 15(*d*) illustrates a phase angle spectrum acquired together with the energy spectrum in FIG. 15(*a*), i.e. for a flow rate of 300 ml/min. The graph in FIG. 15(*d*) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library may be used to generate a temporal reference profile. Each energy value in the energy data corresponds to an amplitude of a sinusoid with a given frequency (the frequency associated with the energy value), wherein the phase value for the given frequency indicates the proper phase angle of the sinusoid. This method of preparing the predicted temporal reference profile by combining (typically adding) sinusoids of appropriate frequency, amplitude and phase angle allows the predicted temporal reference profile to include all harmonics of the pump frequency within a desired frequency range.

When a predicted reference profile (temporal or spectral) is to be generated, the reference library is first searched based on a current value of one or more system parameters, such as the current pump frequency. If no exact match is found in the reference library, a combination process may be executed. For example, the two closest matching pump frequencies may be identified in the reference library and the associated energy and phase data may be retrieved and combined. The combination may be done by interpolating the energy data and the phase data, respectively. In the example of FIGS. 15(*a*)-15(*d*), an interpolated energy value may be calculated for each harmonic number, and similarly an interpolated phase value may be calculated for each harmonic number. Any type of interpolation function may be used, be it linear or non-linear.

In the first, second and third embodiments, one and the same pressure sensor is suitably used in both the reference measurement and the actual monitoring process. Alternatively, different pressure sensor units may be used, provided that the pressure sensor units yield identical signal responses with respect to the pump pulses or that the signal responses may be matched using a known mathematical relationship.

To further improve the first, second and third embodiments, the process of generating the predicted reference profile (temporal or spectral) may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

Figure 15A:
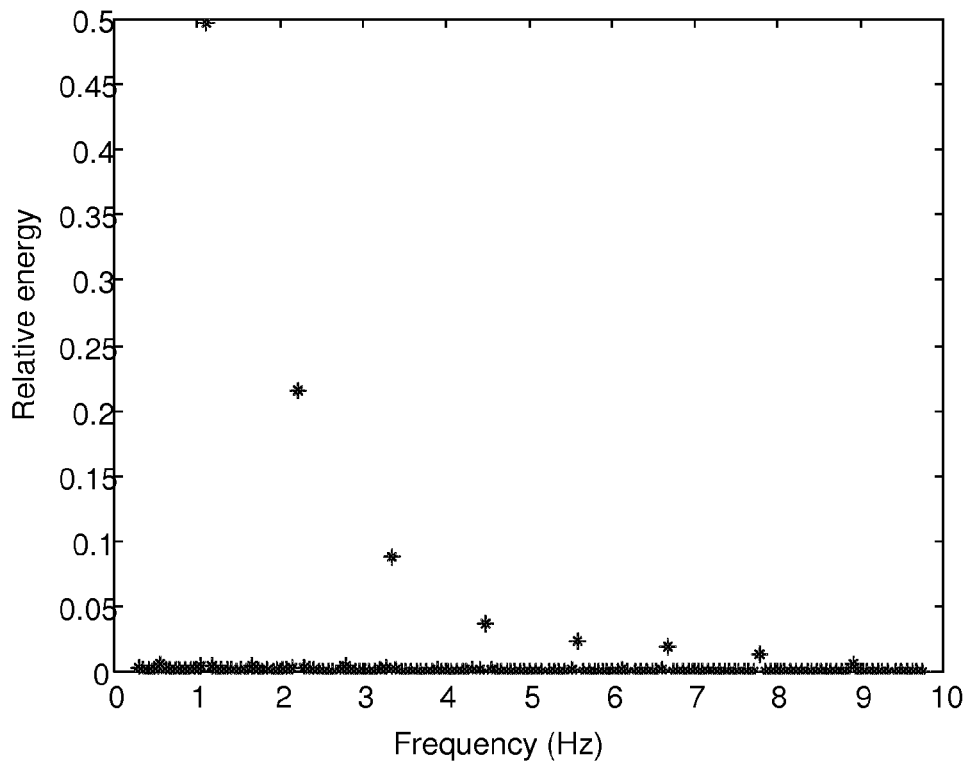
FIG. 15($a$) represents a frequency spectrum of pump pulses at one flow rate, FIG. 15($b$) represents corresponding frequency spectra for three different flow rates, wherein each frequency spectrum is given in logarithmic scale and mapped to harmonic numbers, FIG. 15($c$) is a plot of the data in FIG. 15($b$) in linear scale, and FIG. 15($d$) is a phase angle spectrum corresponding to the frequency spectrum in FIG. 15($a$).
Figure 15B:
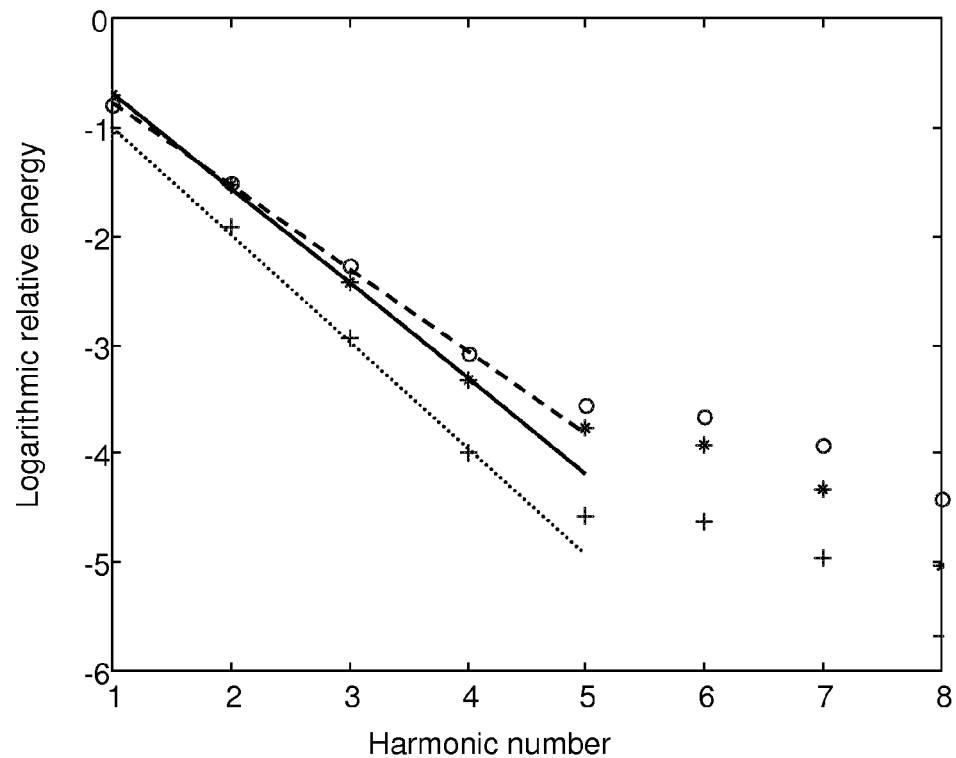
Figure 15C:
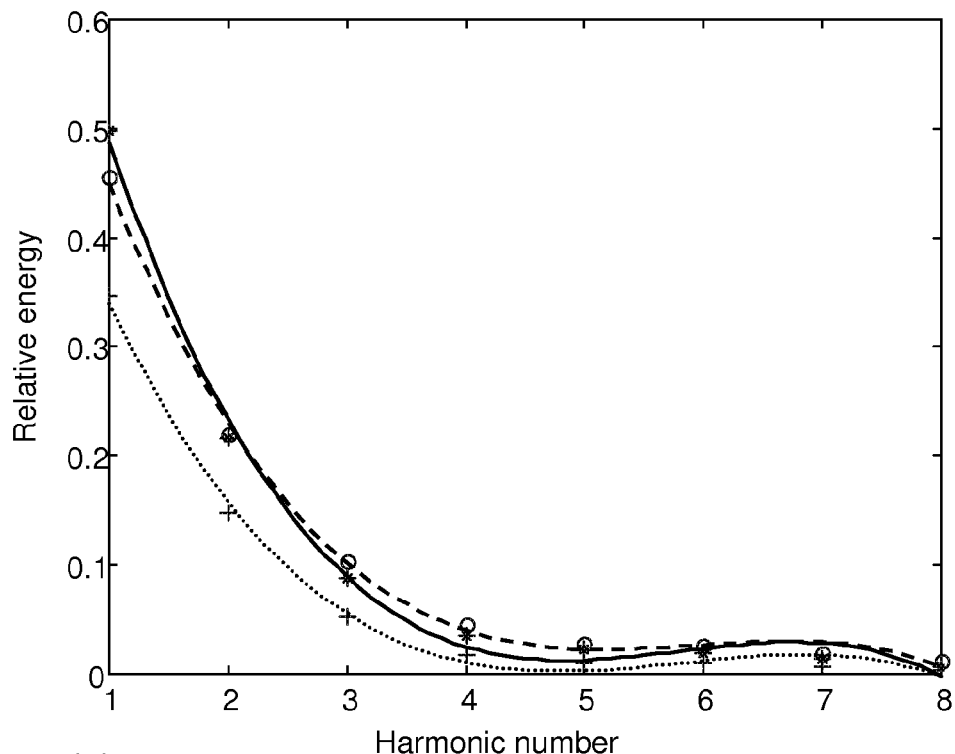
Figure 15D:
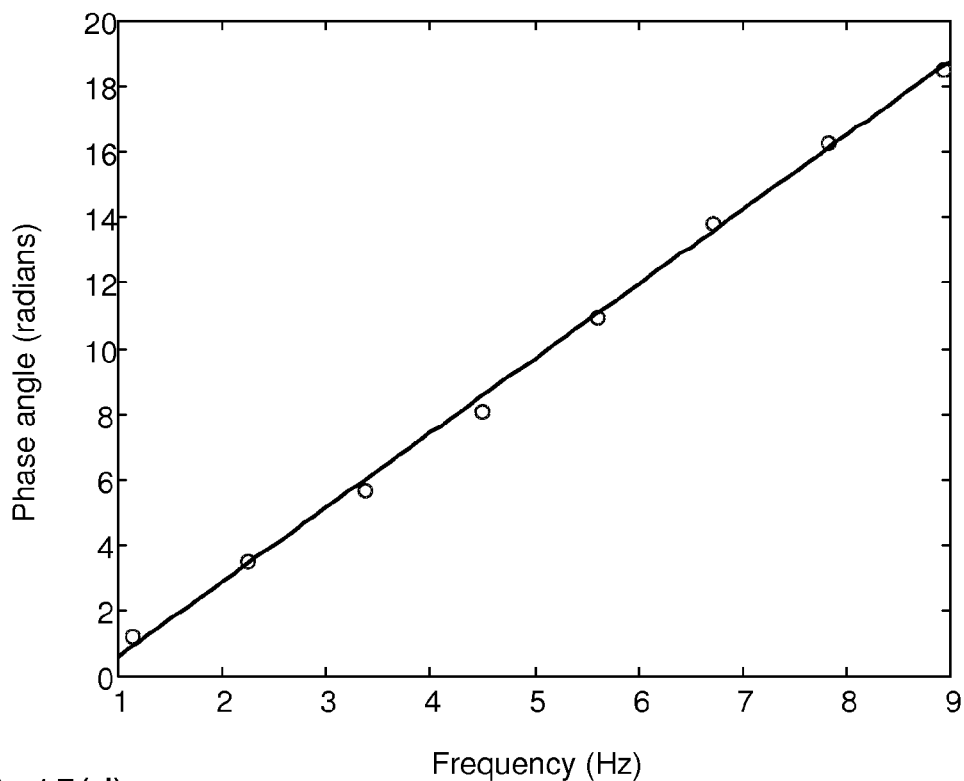

In further variations, the second and third embodiments may be combined, e.g. in that the reference library stores not only energy and phase data, but also temporal library profiles, in association with system parameter value(s). When an exact match is found in the library, the temporal library profile is retrieved from the library and used as the predicted reference profile, otherwise the predicted reference profile is obtained by retrieving and combining (e.g. interpolating) the energy and phase data, as in the third embodiment. In a variant, the predicted reference profile u(n) at the current pump frequency v is obtained by:

$$u(n) = r_i(n) - r'_i(n) + r'(n),$$

wherein $r_i(n)$ denotes a temporal library profile that is associated with the closest matching pump frequency $v_i$ in the reference library, $r'_i(n)$ denotes a temporal reference profile that is reconstructed from the energy and phase data associated with the closest matching pump frequency $v_i$ in the reference library, and $r'(n)$ denotes an estimated temporal reference profile at the current pump frequency v. The estimated temporal reference profile $r'(n)$ may be obtained by applying predetermined functions to estimate the energy and phase data, respectively, at the current pump frequency v based on the energy and phase data associated with the closest matching pump frequency $v_i$. With reference to FIGS. 15(b)-15(c), such a predetermined function may thus represent the change in energy data between different flow rates. Alternatively, the estimated temporal reference profile $r'(n)$ may be obtained by retrieving and combining (e.g. interpolating) energy and phase data for the two closest matching pump frequencies $v_i$ and $v_j$ as in the third embodiment.

As an alternative to the use of reference measurements, the reference profile may be obtained directly through simulations, i.e. calculations using a mathematical model of the extracorporeal circuit 20, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model may be anything from a complete physical description of the system to a simple function. In one example, such a simple function may convert data on the instantaneous angular velocity of the pump rotor 3' to a reference profile, using empirical or theoretical data. Such data on the instantaneous angular velocity might be obtained from the pump sensor 26 in FIG. 1.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

VII. Time-Domain Filtering

By filtering the pressure signal in the time-domain, it is possible to essentially eliminate physiological pulses, even if the pump pulses and physiological pulses overlap or nearly overlap in the frequency domain. A frequency overlap is not unlikely, e.g. if one or both of the pump pulses and the physiological pulses is made up of a combination of frequencies or frequency ranges. By "essentially eliminating" is meant that the physiological pulses are removed from the pressure signal to such an extent that the pump pulses may be detected and analysed for the purpose of detecting fault conditions.

Furthermore, the frequency, amplitude and phase content of the pump pulses and the physiological pulses may vary over time. For example, such variations are known to occur in the heart rhythm. In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Any frequency overlap may make it difficult to remove physiological pulses by conventional filtering in the frequency domain. Furthermore, frequency variations may make it even harder to successfully remove physiological pulses, since the frequency overlap may vary over time. Even in the absence of any frequency overlap, frequency variations may make it difficult to define filters in the frequency domain.

Still further, the time domain filtering may make it possible to remove individual physiological pulses, and may thus improve the response time compared to filtering in the frequency domain, which may need to operate on a sequence of pump pulses and physiological pulses in the pressure signal.

There are several different ways of removing one or more physiological pulses from the pressure signal, using either a temporal reference profile of the pump pulses (i.e. the predicted reference profile u(n) obtained as described in Section VI above) or a temporal reference profile of the physiological pulses (denoted "predicted physiological profile" in the following). Here, two different removal processes will be described: Single Subtraction and Adaptive Filtering. Of course, the description of removal processes and their implementations is not comprehensive (neither of the different alternatives, nor of the implementations), which is obvious to a person skilled in the art.

Depending on implementation, the predicted reference profile/predicted physiological profile may be input to the removal process as is, or it may be duplicated to construct an input signal of suitable length for the removal process.

Single Subtraction

In this removal process, a single predicted physiological profile is subtracted from the pressure signal. The predicted physiological profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted physiological profile is shifted in time based on physiological timing information that indicates the expected timing of the physiological pulse(s) in the pressure signal. The physiological timing information may be obtained in any one of a plurality of different ways. For example, the physiological timing information may be extracted from the output signal of a pulse sensor coupled to the patient. The output signal may indicate individual physiological pulses or an average time between physiological pulses. In either case, a predicted time point for a physiological pulse in the pressure signal may be calculated based on the output signal of the pulse sensor and a known difference in arrival time between the pulse sensor and the pressure sensor(s) that generates the pressure signal(s). The pulse sensor may e.g. be a pulse watch, a pulse oximeter, an electrocardiograph, a myograph, a capnograph, etc. Alternatively, the physiological timing information may be obtained based on the relative timing of previously detected physiological pulses in the pressure signal. For example, the time difference between the two most recently detected physiological pulses may be used to predict the time point for subsequent physiological pulse(s). Alternatively or additionally, to potentially improve the precision of the physiological timing information, the physiological timing information may be obtained by intermittently stopping the blood pump, while identifying at least one physiological pulse in the pressure signal.

One potential limitation of this removal process is that the relationship between different frequencies in the predicted physiological profile is always the same, since the process only shifts and scales the predicted physiological profile. Furthermore, this removal process may benefit from having access to the physiological timing information, which may not be available. To overcome these limitations, adaptive filtering may be used and designed to operate on the predicted reference profile, i.e. the predicted pump profile, instead of the predicted physiological profile, e.g. as described in the following.

Adaptive Filtering

Figure 16:
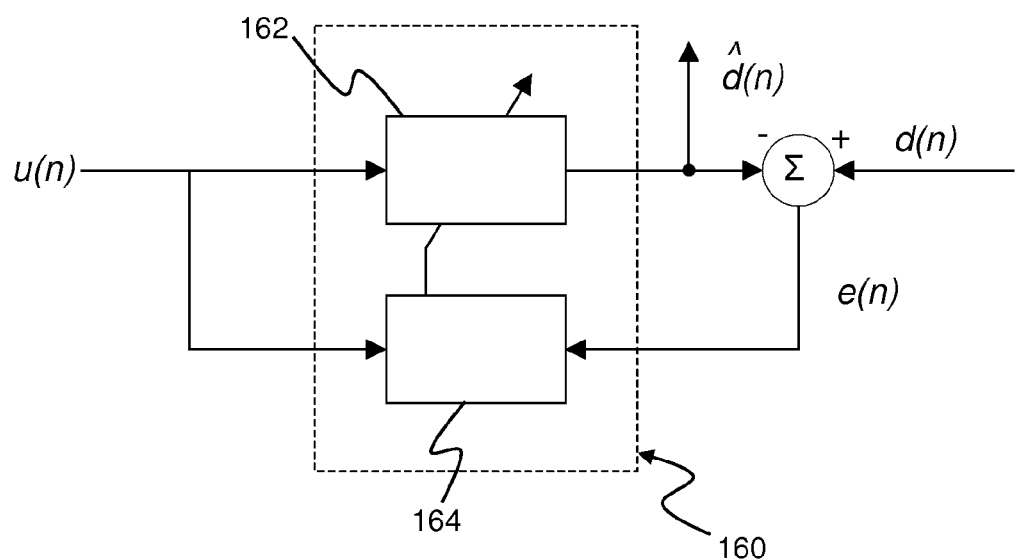
FIG. 16 is schematic view of an adaptive filter structure operable to filter a pressure signal based on a predicted reference profile.

FIG. 16 is a schematic overview of an adaptive filter 160 and an adaptive filter structure which is designed to receive the predicted reference profile u(n) and a pressure signal d(n), and to output an estimation signal $\hat{d}(n)$ which forms the aforesaid monitoring signal in which the physiological pulses are removed.

Adaptive filters are well-known electronic filters (digital or analog) that self-adjust their transfer function according to an optimizing algorithm. Specifically, the adaptive filter 160 includes a variable filter 162, typically a finite impulse response (FIR) filter of length M with filter coefficients w(n).

Even if adaptive filters are known in the art, they are not readily applicable to cancel the physiological pulses in the pressure signal d(n). In the illustrated embodiment, this has been achieved by inputting the predicted reference profile u(n) to the variable filter 162, which processes the predicted reference profile u(n) to generate the estimation signal $\hat{d}(n)$, and to an adaptive update algorithm 164, which calculates the filter coefficients of the variable filter 162 based on the predicted reference profile u(n) and an error signal e(n). The error signal e(n) is given by the difference between the pressure signal d(n) and the estimation signal $\hat{d}(n)$.

Basically, the calculation of the error signal e(n) involves a subtraction of the predicted reference profile u(n) from the pressure signal d(n), since each of the filter coefficients operates to shift and possibly re-scale the amplitude of the predicted reference profile u(n). The estimation signal $\hat{d}(n)$, which is subtracted from the pressure signal d(n) to generate the error signal e(n), is thus formed as a linear combination of M shifted and amplitude-scaled predicted reference profiles u(n).

The adaptive update algorithm 164 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 164, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum.

In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\},$$

and in a deterministic description of the signal the cost function may typically be according to, $$J(n)=\Sigma e^2(n).$$

The physiological pulses will be removed in the estimation signal $\hat{d}(n)$ when the error signal e(n) (cost function J(n)) is minimized. Thus, the error signal e(n) will be cleaned from pump pulses while retaining the physiological pulses, once the adaptive filter 160 has converged and reached the minimum error.

In order to obtain the optimal filter coefficients w(n) for the variable filter 162, the cost function J needs to be minimized with respect to the filter coefficients w(n). This may be achieved with the cost function gradient vector $\nabla J$, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $$w=[w_0 w_1 \ldots w_{M-1}]^T M\times 1.$$

Furthermore, the gradient vector $\nabla J$ points in the direction in which the cost is growing the fastest. Thus, the filter coefficients are corrected in the direction opposite to the gradient, where the length of the correction is influenced through the step size parameter $\mu$. There is always a risk for the Steepest Descent algorithm to diverge, since the algorithm contains a feedback. This sets boundaries on the step size parameter $\mu$ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted reference profile u(n), given by $$R = E[\bar{u}(n)\bar{u}^T(n)] = \begin{bmatrix} r(0) & r(1) & \ldots & r(M-1) \\ r(1) & r(0) & & r(M-2) \\ \vdots & \vdots & \ddots & \vdots \\ r(M-1) & r(M-2) & \ldots & r(0) \end{bmatrix},$$

where $\bar{u}(n)$ is given by, $$\bar{u}(n)=[u(n)u(n-1)\ldots u(n-M+1)]^T M\times 1.$$

If the mean squared error (MSE) cost function (defined by $J=E\{|e(n)|^2\}$) is used, it may be shown that the filter coefficients are updated according to, $$w(n+1)=w(n)+\mu E[\bar{u}(n)e(n)],$$

where $e(n)$ is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm may adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted reference profile $u(n)$, i.e., the gradient noise is amplified when the predicted reference profile is strong. One solution to this problem is to normalize the update of the filter coefficients with $$\|\bar{u}(n)\|^2=\bar{u}^T(n)\bar{u}(n).$$

The new update equation of the filter coefficients is called the Normalized LMS, and is given by $$w(n+1)=w(n)+\frac{\tilde{\mu}}{a+\|\bar{u}(n)\|^2}\bar{u}(n)e(n),$$

where $0<\tilde{\mu}<2$, and a is a positive protection constant.

There are many more different alternatives to the LMS algorithm, where the step size is modified. One of them is to use a variable adaptation step, $$w(n+1)=w(n)+\alpha(n)\bar{u}(n)e(n),$$

where $\alpha(n)$ for example may be, $$\alpha(n)=\frac{1}{n+c},$$

where c is a positive constant. It is also possible to choose independent adaptation steps for each filter coefficient in the LMS algorithm, e.g., according to, $$w(n+1)=w(n)+A\bar{u}(n)e(n),$$

where A is given by, $$A=\begin{bmatrix} \alpha_1 & 0 & 0 & \ldots & 0 \\ 0 & \alpha_2 & 0 & \ldots & 0 \\ 0 & 0 & \alpha_3 & \ldots & 0 \\ \vdots & \vdots & \vdots & \ddots & \vdots \\ 0 & 0 & 0 & \ldots & \alpha_M \end{bmatrix}.$$

If instead the following cost function $$J(n)=E\{|e(n)|\}$$

is used, then the update equation becomes $$w(n+1)=w(n)+\alpha\,\mathrm{sign}[e(n)]\bar{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance a was added to the predicted reference profile $u(n)$. As a result, the uncertainty in the input signal $u(n)$ is increased, which tends to hold the filter coefficients back. The Leaky LMS is preferably used when R, the correlation matrix of $u(n)$, has one or more eigenvalues equal to zero. However, in systems without noise, the Leaky LMS makes performance poorer. The update equation of the filter coefficients for the Leaky LMS is given by, $$w(n+1)=(1-\mu\alpha)w(n)+\mu\bar{u}(n)e(n).$$

Instead of minimizing the MSE cost function as above, the Recursive Least Squares (RLS) adaptive filter algorithm minimizes the following cost function $$J(n)=\sum_{i=1}^{n}\lambda^{n-i}|e(i)|^2,$$

where $\lambda$, is called forgetting factor, $0<\lambda\le 1$, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M\times M}$ is the identity matrix $M\times M$, given according to $$k(n)=\frac{\lambda^{-1}P(n-1)\bar{u}(n)}{1+\lambda^{-1}\bar{u}^T(n)P(n-1)\bar{u}(n)}$$

$$\xi(n)=d(n)-w^T(n-1)\bar{u}(n)$$

$$w(n)=w(n-1)+k(n)\xi(n)$$

$$P(n)=\lambda^{-1}P(n-1)-\lambda^{-1}k(n)\bar{u}^T(n)P(n-1),$$

where $\delta$ is a small positive constant for high signal-to-noise ratio (SNR), and a large positive constant for low SNR, $\delta \ll 0.01\sigma_u^2$, and $\xi(n)$ corresponds to e(n) in the preceding algorithms. During the initialization phase the following cost function $$J(n) = \sum_{i=1}^{n} \lambda^{n-i}|e(i)|^2 + \delta\lambda^n \|w(n)\|^2,$$

is minimized instead, due to the use of the initialization $P(0)=\delta^{-1}1$. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different $\lambda$ and $\delta$, which may be combined in order to improve performance, i.e., $\lambda=1$ may also be used in the algorithm (steady state solution) with many different $\delta$:s.

It should be noted that both the LMS algorithm and the RLS algorithm may be implemented in fixed-point arithmetic, such that they may be run on a processor that has no floating point unit, such as a low-cost embedded microprocessor or microcontroller.

Irrespective of implementation, the performance of the adaptive filter 160 may be further improved by switching the adaptive filter 160 to a static mode, in which the update algorithm 164 is disabled and thus the filter coefficients of the filter 162 are locked to a current set of values. The switching of the adaptive filter 160 may be controlled by an external process that analyses the physiological pulses in the error signal e(n), typically in relation to pump pulse data. The pump pulse data may be obtained from the pressure signal, a reference signal (see above), a dedicated pulse sensor, a control unit for the blood pump, etc. The adaptive filter 160 may be switched into the static mode if the external process reveals that the rate of physiological pulses starts to approach the rate of the pump pulses and/or that the amplitude of the physiological pulses is very weak (in relation to an absolute limit, or in relation to a limit given by the amplitude of the pump pulses). The adaptive filter may remain in static mode for a predetermined time period, or until released by the external process.

In a variant, the above-mentioned predicted physiological profile is used as input signal to the adaptive filter 160 (instead of the predicted reference profile), and the monitoring signal is formed by the error signal e(n) (instead of the estimation signal $\hat{d}(n)$). The foregoing discussion with respect to adaptive filters is equally applicable to this variant.

It should be realized from the foregoing that the adaptive filter 160 (in either variant) also generates a signal which contains physiological pulses and is essentially free of pump pulses. In one implementation of the monitoring process in FIG. 3, the first integrity check 32 is configured to identify a fault condition in the connection system based on this signal, and the decision step 34 is configured to switch to the pump profile analysis 36 if the physiological pulses in this signal are too weak or too close in frequency to the pump pulses.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, in all of the different above-described monitoring applications, the accuracy of the monitoring may be improved by subjecting the measurement data to a signal enhancement process, as part of the process for generating the monitoring signal/evaluation segments. Such a signal enhancement process may involve subjecting the measurement data to a low-pass filtering. However, a more significant improvement in SNR of the monitoring signal/evaluation segment may be achieved by averaging several consecutive pump pulses in the measurement data, based on the above-mentioned pump timing information, which indicates the predicted timing of pump pulses in the measurement data. Such a signal enhancement process would thus involve using the predicted timing to identify a set of pump pulse segments in the measurement data, aligning the pump pulse segments in the time domain based on the predicted timing, and generating an average representation by summing the aligned signal values for each time value in the time domain. Optionally, the average representation may be normalized by the number of pump pulse segments to generate a true average. In an alternative, the average representation is generated by taking the median of the aligned signal values for each time value in the time domain. The skilled person realizes that there are further equivalent ways to process the aligned signal values to achieve a signal enhancement. The average representation may then be used as the above-mentioned evaluation segment, or the evaluation segment may be extracted from a time window within the average representation. In a variant, the above-described signal enhancement process may involve using the pump timing information to identify and average pump pulse segments from measurement data acquired from different pressure sensors. Thus, the monitoring signal/evaluation segments may be generated based on plural time windows in measurement data from a single pressure sensor and/or from one or more time windows in measurement data from different pressure sensors.

In another example, one or more embodiments for monitoring fault conditions in the connection system C (e.g. as disclosed in Sections II-IV) may be combined with an embodiment for monitoring the condition of the blood pump (e.g. as disclosed in Section V). For example, it is possible that an indication of a fault condition in the connection system C is actually caused by a fault condition in the blood pump. Thus, it may be advantageous to check the condition of the blood pump, whenever the monitoring indicates a fault condition in the connection system C. If the check reveals minor changes in the blood pump (e.g. calibration changes), the surveillance device may be caused to generate/obtain a new reference profile of the pump pulses (e.g. according to Section VI above). If the check indicates a major fault, an alarm may be given to indicate a fault condition in the blood pump.

Still further, the extracorporeal circuit may include any type of pumping device, not only rotary peristaltic pumps as disclosed above, but also other types of positive displacement pumps, such as linear peristaltic pumps, diaphragm pumps, as well as centrifugal pumps.

Embodiments of the invention are also applicable when the connection system comprises a single access device, such as in so-called single needle treatment.

The inventive technique is applicable to all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The above-described embodiments may also be applicable to monitoring of fault conditions in fluid containing systems containing other liquids than blood. Likewise, the connection system need not be provided in relation to a human, but may be provided in relation to any other type of fluid containing system.

In one example, the connection system is provided between a blood processing circuit and a container/machine, wherein blood is pumped from one container/machine through a blood processing device in the blood processing circuit and back to the container/machine, or to another container/machine downstream of the blood processing device. The blood processing device may be any known device configured to modify and/or analyse the blood.

In a further example, the connection system is provided between a dialyser and a reprocessing system, which reprocesses the dialyser by pumping water, optionally together with suitable chemicals through the dialyser. An example of a dialyser reprocessing system is known from US2005/0051472.

In another example, the connection system is provided between a dialysate supply and a dialysate regeneration system, which circulates dialysate from the dialysate supply through a dialysate regeneration device and back to the supply. An example of a dialysate regeneration device is known from WO 05/062973.

In yet another example, the connection system is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the connection system is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the connection system is provided in an arrangement for purifying water, which pumps water from a supply through a purifying device. The purifying device may use any known water purification technique, e.g. reverse osmosis, deionization or carbon absorption.

In another example, the connection system is provided in an arrangement for providing purified water to a dialysis machine, e.g. to be used in the preparation of dialysis solution therein.

In all of these examples, and in other applications related to medical treatment of human or animal patients, it may be vital to monitor the integrity of the connection system and/or the operation of pumping devices. Such monitoring may be accomplished according to the embodiments disclosed herein.

The monitoring process may be executed by a surveillance device (cf. 25 in FIG. 1), which may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The surveillance device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software, and the adjustment factors, may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The surveillance device may include one or more communication interfaces, such as a serial interface, a parallel interface, a USB interface, a wireless interface, a network adapter, etc, as well as one or more data acquisition devices, such as an A/D converter. The special-purpose software may be provided to the surveillance device on any suitable computer-readable medium, including a record medium, a read-only memory, or an electrical carrier signal.

It is also conceivable that some (or all) method steps are fully or partially implemented by dedicated hardware, such as an FPGA, an ASIC, or an assembly of discrete electronic components (resistors, capacitors, operational amplifier, transistors, filters, etc), as is well-known in the art.

In the following, a set of items are recited to summarize some aspects and embodiments of the invention as disclosed in the foregoing.

Item 1. A method for detecting a fault condition in a fluid connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said method comprising:

generating a time-dependent monitoring signal based on measurement data obtained from said at least one pressure sensor (4a-4c), such that the monitoring signal at least comprises one or more first pulses;

processing the monitoring signal to calculate a parameter value which is indicative of the shape of at least part of a first pulse in the monitoring signal, and evaluating the parameter value for detection of said fault condition.

Item 2. The method of item 1, wherein the step of processing comprises: extracting shape-indicative data from the monitoring signal and comparing the shape-indicative data to reference data.

Item 3. The method of item 2, wherein the shape-indicative data comprises signal values in the monitoring signal, and the reference data comprises a temporal reference profile (u(n)).

Item 4. The method of item 3, wherein said comparing comprises obtaining timing information indicative of the timing of at least one first pulse in the monitoring signal, and using the timing information to align the signal values in the monitoring signal with the temporal reference profile (u(n)).

Item 5. The method of item 2, wherein the shape-indicative data is extracted by an analysis of the frequency content of the monitoring signal, and wherein the reference data is indicative of an amplitude spectrum.

Item 6. The method of item 5, wherein the shape-indicative data is further extracted by an analysis of the phase content of the monitoring signal, and wherein the reference data is further indicative of a phase spectrum.

Item 7. The method of any one of items 2-6, wherein the parameter value is indicative of a similarity or a deviation between the shape-indicative data and the reference data.

Item 8. The method of any one of items 2-7, wherein the reference data represents the shape of said at least part of a first pulse in the monitoring signal at said fault condition.

Item 9. The method of any one of items 2-7, wherein the reference data represents the shape of said at least part of a first pulse in the monitoring signal in absence of said fault condition.

Item 10. The method of any one of items 2-9, further comprising the step of obtaining a current value of one or more system parameters of the first fluid containing system (20), and the step of obtaining the reference data as a function of the current value.

Item 11. The method of item 10, wherein said step of obtaining the reference data comprises: identifying, based on the current value, one or more reference profiles ($r_1(n)$, $r_2(n)$) in a reference database; and obtaining the reference data based on said one or more reference profiles ($r_1(n)$, $r_2(n)$).

Item 12. The method of item 11, wherein each reference profile ($r_1(n)$, $r_2(n)$) in the reference database is obtained by a reference measurement in the fluid containing system for a respective value of said one or more system parameters.

Item 13. The method of item 10, wherein said step of obtaining the reference data comprises: identifying, based on the current value, one or more combinations of energy and phase angle data in a reference database; and obtaining reference data based on said one or more combinations of energy and phase angle data.

Item 14. The method of item 13, wherein the reference data is obtained by combining a set of sinusoids of different frequencies, wherein the amplitude and phase angle of each sinusoid is given by said one or more combinations of energy and phase angle data.

Item 15. The method of item 10, wherein said step of obtaining the reference data comprises: inputting the current value into an algorithm which calculates the response of said at least pressure sensor (4a-4c) based on a mathematical model of the first fluid containing system (20).

Item 16. The method of any one of items 10-15, wherein said one or more system parameters is indicative of the rate of first pulses in the first fluid containing system (20).

Item 17. The method of any preceding item, wherein the step of generating the monitoring signal comprises: deriving, based on timing information indicative of the timing of the first pulses in the measurement data, a set of signal segments in the measurement data; and aligning and adding the signal segments, based on the timing information, to generate the monitoring signal.

Item 18. The method of any preceding item, wherein the step of generating the monitoring signal comprises: filtering said measurement data for removal of said second pulses.

Item 19. The method of item 18, wherein the first fluid containing system is an extracorporeal blood flow circuit (20), wherein the second fluid containing system is a vascular system of a subject, wherein the fluid connection system (C) comprises an access device (1; 14) for connection to an access point of the vascular system, wherein the fault condition is a disconnection of the access device (1; 14) from the access point or from the extracorporeal blood flow circuit (20).

Item 20. The method of item 19, wherein said disconnection is indicated by absence of a deformation in said shape of at least part of the first pulse, which deformation is caused by pressure variations generated in said access point of the vascular system by the first pulses.

Item 21. The method of any one of items 18-20, wherein the step of filtering comprises: obtaining a second pulse profile which is a predicted temporal signal profile of at least one second pulse, and filtering the measurement data in the time-domain, using the second pulse profile, to essentially eliminate the second pulses while retaining the first pulses.

Item 22. The method of item 21, wherein the step of filtering comprises subtracting the second pulse profile from the measurement data.

Item 23. The method of item 22, wherein the step of subtracting is preceded by an adjustment step, in which at least one of the amplitude, the time scale and the phase of the second pulse profile is adjusted with respect to the measurement data.

Item 24. The method of item 23, wherein the adjustment step comprises minimizing a difference between the second pulse profile and the measurement data.

Item 25. The method of any one of items 21-24, wherein the step of filtering comprises: supplying the second pulse profile as input to an adaptive filter (160); calculating an error signal (e(n)) between the measurement data (d(n)) and an output signal ($\hat{d}(n)$) of the adaptive filter (160); and providing the error signal (e(n)) as input to the adaptive filter (160), whereby the adaptive filter (160) is arranged to essentially eliminate the second pulses in the error signal (e(n)).

Item 26. The method of any one of items 18-20, wherein the step of filtering comprises: obtaining a first pulse profile (u(n)) which is a predicted temporal signal profile of at least one first pulse, and supplying the first pulse profile (u(n)) as input to an adaptive filter (160); calculating an error signal (e(n)) between the measurement data (d(n)) and an output signal ($\hat{d}(n)$) of the adaptive filter (160); and providing the error signal (e(n)) as input to the adaptive filter (160), whereby the adaptive filter (160) is arranged to essentially eliminate the second pulses in the output signal ($\hat{d}(n)$). The adaptive filter (160) may be operated to generate the estimation signal ($\hat{d}(n)$) as a linear combination of M shifted first pulse profiles (u(n)), and specifically the adaptive filter (160) may be operated to linearly combine M instances of the first pulse profile (u(n)), which are properly adjusted in amplitude and phase by the adaptive filter (30).

Item 27. The method of item 26, wherein the adaptive filter (160) comprises a finite impulse response filter (162) with filter coefficients that operate on the first pulse profile (u(n)) to generate the output signal ($\hat{d}(n)$), and an adaptive algorithm (164) which optimizes the filter coefficients as a function of the error signal (e(n)) and the first pulse profile (u(n)).

Item 28. The method of item 26 or 27, further comprising the step of controlling the adaptive filter (160) to lock the filter coefficients, based on a comparison of the rate and/or amplitude of the second pulses to a limit value.

Item 29. The method of any one of items 26-28, wherein the first pulse profile (u(n)) is obtained in a reference measurement in the first fluid containing system (20), wherein the reference measurement comprises the steps of: operating the first pulse generator (3) to generate at least one first pulse, and obtaining the first pulse profile (u(n)) from a reference signal generated by a reference pressure sensor (4a-4c) in the first fluid containing system (20).

Item 30. The method of item 29, wherein the first pulse generator (3) is operated to generate a sequence of first pulses during the reference measurement, and wherein the first pulse profile (u(n)) is obtained by identifying and averaging a set of first pulse segments in the reference signal.

Item 31. The method of item 29 or 30, wherein the reference measurement is effected intermittently during operation of the first fluid containing system (20) to provide an updated first pulse profile (u(n)).

Item 32. The method of any one of items 29-31, wherein said at least one pressure sensor (4a-4c) is used as said reference pressure sensor.

Item 33. The method of any one of items 29-32, wherein the first fluid containing system (20) is operated, during the reference measurement, such that the reference signal contains a first pulse and no second pulse.

Item 34. The method of any preceding item, wherein said steps of processing and evaluating are conditioned upon a preceding step of detecting that said second pulses are essentially absent in said measurement data.

Item 35. The method of any one of items 1-33, wherein said steps of calculating and evaluating are conditioned upon a preceding step of detecting that a frequency component of the first pulses essentially coincides with a frequency component of the second pulses.

Item 36. The method of any preceding item, further comprising a step of processing the monitoring signal for detection of a fault condition in the first pulse generator (3).

Item 37. The method of item 36, wherein the step of processing the monitoring signal for detection of a fault condition in the first pulse generator (3) is initiated by a detection of the fault condition in the fluid connection system (C).

Item 38. The method of any preceding item, wherein the first fluid containing system is an extracorporeal blood processing system (20), and wherein the second fluid containing system is a vascular system of a subject, wherein the fluid connection system (C) comprises a first access device (1) for connection to an arterial access point of the vascular system and a second access device (14) for connection to a venous access point of the vascular system, and wherein the extracorporeal blood processing system (20) comprises a blood processing device (6) and a pumping device (3) which is arranged to pump blood from the vascular system via the first access device (1) through the blood processing device (6) and back to the vascular system via the second access device.

Item 39. The method of item 38, wherein the second pulses originate from one or more repetitive physiological pulse generators in the subject.

Item 40. The method of item 38 or 39, wherein the fault condition comprises at least one of: a disconnection of one of the first and second access devices (1, 14) from the vascular system or from the extracorporeal system (20); a connection of the first and second access devices (1, 14) to the venous and arterial access points, respectively; an occlusion of the fluid path through one of the first and second access devices (1, 14); and an infiltration in tissue surrounding one of the venous and arterial access points.

Item 41. The method of any one of items 38-40, wherein said at least one pressure sensor (4c) is arranged intermediate the second access device (14) and the pumping device (3).

Item 42. The method of any preceding item, wherein each first pulse corresponds to a pump stroke of a pumping device (3) in the first fluid containing system (20).

Item 43. The method of any preceding item, wherein the pumping device (3) is a peristaltic pump and each pressure pulse is generated while a rotating roller (3a, 3b) of the peristaltic pump engages a tubing segment to displace blood through the first fluid containing system (20).

Item 50. A computer program product comprising instructions for causing a computer to perform the method of any one of items 1-43.

Item 60. A device for detecting a fault condition in a fluid connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said device comprising:

means (29) for generating a time-dependent monitoring signal based on measurement data obtained from said at least one pressure sensor (4a-4c), such that the monitoring signal at least comprises one or more first pulses;

means (29) for processing the monitoring signal to calculate a parameter value which is indicative of the shape of at least part of a first pulse in the monitoring signal, and means (29) for evaluating the parameter value for detection of said fault condition.

Embodiments of the device as set forth in item 60 may correspond to the embodiments of the method as set forth in items 2-43.

Item 61. A device for detecting a fault condition in a fluid connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said device comprising:

an input (28) for obtaining measurement data from said at least one pressure sensor (4a-4c), and a signal processor (29) connected to said input and being configured to generate a time-dependent monitoring signal based on the measurement data such that the monitoring signal at least comprises one or more first pulses, to process the monitoring signal for calculation of a parameter value which is indicative of the shape of at least part of a first pulse in the monitoring signal, and to evaluate the parameter value for detection of said fault condition.

Embodiments of the device as set forth in item 61 may correspond to the embodiments of the method as set forth in items 2-43.

Item 70. A method for detecting a fault condition in a pumping device (3) included in an extracorporeal blood treatment system (20), wherein the extracorporeal blood treatment system (20) is adapted for connection to a vascular system of a subject such that the pumping device (3) pumps blood from the vascular system through a blood treatment device (6) back to the vascular system, and wherein at least one pressure sensor (4a-4c) is arranged in the extracorporeal blood treatment system (20) to detect first pulses originating from the pumping device (3) and second pulses originating from a physiological pulse generator in the subject, said method comprising:

generating a time-dependent monitoring signal based on measurement data obtained from said at least one pressure sensor (4a-4c), such that the monitoring signal comprises one or more first pulses and no second pulses;

processing the monitoring signal to calculate a parameter value which is indicative of the shape of at least part of a first pulse in the monitoring signal; and evaluating the parameter value for detection of said fault condition.

Item 71. The method of item 70, wherein the step of generating comprises filtering the measurement data for removal of the second pulses.

Item 72. The method of item 70, wherein the step of generating comprises operating the extracorporeal blood treatment system (20) such that the second pulses are prevented from reaching said at least one pressure sensor (4a-4c).

Item 73. The method of any one of items 70-72, wherein the fault condition comprises a loss of occlusion in the pumping device (3).

Item 80. A computer program product comprising instructions for causing a computer to perform the method of any one of items 70-73.

Item 90. A device for detecting a fault condition in a pumping device (3) included in an extracorporeal blood treatment system (20), wherein the extracorporeal blood treatment system (20) is adapted for connection to a vascular system of a subject such that the pumping device (3) pumps blood from the vascular system through a blood treatment device (6) back to the vascular system, and wherein at least one pressure sensor (4a-4c) is arranged in the extracorporeal blood treatment system (20) to detect first pulses originating from the pumping device (3) and second pulses originating from a physiological pulse generator in the subject, said device comprising:

means (29) for generating a time-dependent monitoring signal based on measurement data obtained from said at least one pressure sensor (4a-4c), such that the monitoring signal comprises one or more first pulses and no second pulses;

means (29) for processing the monitoring signal to calculate a parameter value which is indicative of the shape of at least part of a first pulse in the monitoring signal; and means (29) for evaluating the parameter value for detection of said fault condition.

Embodiments of the device as set forth in item 90 may correspond to the embodiments of the method as set forth in items 71-73.

Item 91. A device for detecting a fault condition in a pumping device (3) included in an extracorporeal blood treatment system (20), wherein the extracorporeal blood treatment system (20) is adapted for connection to a vascular system of a subject such that the pumping device (3) pumps blood from the vascular system through a blood treatment device (6) back to the vascular system, and wherein at least one pressure sensor (4a-4c) is arranged in the extracorporeal blood treatment system (20) to detect first pulses originating from the pumping device (3) and second pulses originating from a physiological pulse generator in the subject, said device comprising:

an input (28) for obtaining measurement data from said at least one pressure sensor (4a-4c), and a signal processor (29) connected to said input and being configured to generate a time-dependent monitoring signal based on measurement data obtained from said at least one pressure sensor (4a-4c), such that the monitoring signal comprises one or more first pulses and no second pulses, to process the monitoring signal to calculate a parameter value which is indicative of the shape of at least part of a first pulse in the monitoring signal, and to evaluate the parameter value for detection of said fault condition.

Embodiments of the device as set forth in item 91 may correspond to the embodiments of the method as set forth in items 71-73.

The invention claimed is:

1. A method for detecting and responding to a fault condition in a pumping device included in an extracorporeal blood treatment system, said method comprising:

obtaining measurement data by detecting pulses in the extracorporeal blood treatment system using at least one pressure sensor arranged in the extracorporeal blood treatment system, wherein the pulses comprises first pulses originating from the pumping device of the extracorporeal blood treatment system and second pulses originating from a physiological pumping device in a subject connected to the extracorporeal blood treatment system;

generating a time-dependent monitoring signal based on the measurement data obtained from the at least one pressure sensor, wherein the monitoring signal comprises one or more of the first pulses and none of the second pulses;

processing the monitoring signal to calculate a parameter value which is indicative of the shape of at least part of a first pulse in the monitoring signal;

evaluating the parameter value for detection of a fault condition in the pumping device; and activate an alarm and/or stop the pumping device if a fault condition is detected.

2. The method of claim 1, wherein generating the monitoring signal comprises filtering the measurement data for removal of the second pulses.

3. The method of claim 2, wherein the filtering comprises:

obtaining a second pulse profile which is a predicted temporal signal profile of at least one second pulse, and filtering the measurement data in the time-domain, using the second pulse profile, to essentially eliminate the second pulses while retaining the first pulses.

4. The method of claim 1, wherein generating the monitoring signal comprises operating the extracorporeal blood treatment system such that the second pulses are prevented from reaching said at least one pressure sensor.

5. The method of claim 1, wherein the fault condition comprises a loss of occlusion of a tube by rollers in the pumping device.

6. The method of claim 1, wherein the pumping device comprises a peristaltic pump and each first pulse is generated while a rotating roller of the peristaltic pump engages a tubing segment to displace blood through the extracorporeal blood treatment system.

7. The method of claim 6, wherein the parameter value is calculated as a dispersion measure based on signal values in the measurement data obtained from the at least one pressure sensor in the monitoring signal.

8. The method of claim 6, wherein the parameter value is calculated to represent the symmetry between consecutive first pulses in the monitoring signal.

9. The method of claim 6, wherein the parameter value is calculated by extracting shape-indicative data from the monitoring signal and comparing the shape-indicative data to reference data.

10. The method of claim 9, wherein the shape-indicative data comprises signal values in the monitoring signal, and the reference data comprises a temporal reference profile.

11. The method of claim 9, wherein the shape-indicative data is extracted by an analysis of the frequency content of the monitoring signal, and wherein the reference data is indicative of an amplitude spectrum.

12. The method of claim 9, further comprising obtaining a current value of one or more system parameters of the extracorporeal blood treatment system, and obtaining the reference data as a function of the current value.

13. The method of claim 12, wherein obtaining the reference data comprises: identifying, based on the current value, one or more reference profiles in a reference database; and obtaining the reference data based on the one or more reference profiles.

14. The method of claim 12, wherein the one or more system parameters is indicative of the rate of first pulses in the extracorporeal blood treatment system.

15. A non-transitory computer-readable medium containing computer instructions stored therein for causing a processor to detect a fault condition in a pumping device included in an extracorporeal blood treatment system, the processor detecting and responding to the fault condition by:
generating a time-dependent monitoring signal based on measurement data obtained from said at least one pressure sensor arranged in an extracorporeal blood treatment system configured for connection to a vascular system of a subject, wherein the at least one pressure sensor detects first pulses originating from the pumping device of the extracorporeal blood treatment system pumping blood from the vascular system through a blood treatment device and back to the vascular system, wherein the at least one pressure sensor also detects second pulses originating from a physiological pulse generator in the subject, wherein the monitoring signal comprises one or more first pulses and no second pulses;
processing the monitoring signal to calculate a parameter value which is indicative of the shape of at least part of a first pulse in the monitoring signal;
evaluating the parameter value for detection of a fault condition in the pumping device; and
activating an alarm and/or stopping the pumping device if a fault condition is detected.

16. A device for detecting and responding to a fault condition in a pumping device included in an extracorporeal blood treatment system, wherein the extracorporeal blood treatment system is configured for connection to a vascular system of a subject such that the pumping device pumps blood from the vascular system through a blood treatment device back to the vascular system, and wherein at least one pressure sensor is arranged in the extracorporeal blood treatment system and configured to detect first pulses originating from the pumping device and second pulses originating from a physiological pulse generator in the subject, said device comprising:
means for generating a time-dependent monitoring signal based on measurement data obtained from said at least one pressure sensor, wherein the monitoring signal comprises one or more first pulses and no second pulses;
means for processing the monitoring signal to calculate a parameter value which is indicative of the shape of at least part of a first pulse in the monitoring signal;
means for evaluating the parameter value for detection of a fault condition in the pumping device; and
means for activating an alarm and/or stopping the pumping device if a fault condition is detected.

17. A device for detecting and responding to a fault condition in a pumping device included in an extracorporeal blood treatment system, wherein the extracorporeal blood treatment system is configured for connection to a vascular system of a subject such that the pumping device pumps blood from the vascular system through a blood treatment device back to the vascular system, and wherein at least one pressure sensor is arranged in the extracorporeal blood treatment system and configured to detect first pulses originating from the pumping device and second pulses originating from a physiological pulse generator in the subject, said device comprising:
an input configured to obtain measurement data from said at least one pressure sensor, and
a signal processor connected to said input and being configured to:
generate a time-dependent monitoring signal based on measurement data obtained from said at least one pressure sensor, wherein the monitoring signal comprises one or more first pulses and no second pulses,
process the monitoring signal to calculate a parameter value which is indicative of the shape of at least part of a first pulse in the monitoring signal, and
evaluate the parameter value for detection of a fault condition in the pumping device; and
activate an alarm and/or stop the pumping device if a fault condition is detected.

18. The device of claim 17, wherein the device is configured to filter the measurement data for removal of the second pulses as a part of generating the monitoring signal.

19. The device of claim 18, wherein the device is configured to filter the measurement data by:
obtaining a second pulse profile which is a predicted temporal signal profile of at least one second pulse, and
filtering the measurement data in the time-domain, using the second pulse profile, to essentially eliminate the second pulses while retaining the first pulses.

20. The device of claim 17, wherein the device is configured to generate the monitoring signal by operating the extracorporeal blood treatment system such that the second pulses are prevented from reaching said at least one pressure sensor.

21. The device of claim 17, wherein the pumping device comprises a peristaltic pump and each first pulse is generated while a rotating roller of the peristaltic pump engages a tubing segment to displace blood through the extracorporeal blood treatment system.

22. The device of claim 21, wherein the device is configured to calculate the parameter value as a dispersion measure based on signal values in the measurement data obtained from the at least one pressure sensor in the monitoring signal.

23. The device of claim 21, wherein the device is configured to calculate parameter value to represent the symmetry between consecutive first pulses in the monitoring signal.

24. The device of claim 21, wherein the device is configured to calculate the parameter value by extracting shape-indicative data from the monitoring signal and comparing the shape-indicative data to reference data.

25. The device of claim 24, wherein the shape-indicative data comprises signal values in the monitoring signal, and the reference data comprises a temporal reference profile.

26. The device of claim 24, wherein the shape-indicative data is extracted by an analysis of the frequency content of the monitoring signal, and wherein the reference data is indicative of an amplitude spectrum.

27. The device of claim 24, wherein the device is configured to obtain a current value of one or more system parameters of the extracorporeal blood treatment system, and obtain the reference data as a function of the current value.

28. The device of claim 27, wherein the device is configured to obtain the reference data by: identifying, based on the current value, one or more reference profiles in a reference database; and obtaining the reference data based on the one or more reference profiles.

29. The device of claim 27, wherein the one or more system parameters is indicative of the rate of first pulses in the extracorporeal blood treatment system.

* * * * *